(12) United States Patent
Burkett

(10) Patent No.: US 12,017,052 B2
(45) Date of Patent: Jun. 25, 2024

(54) PAIN-REDUCING INJECTION APPARATUS

(71) Applicant: Joseph Choate Burkett, Addison, TX (US)

(72) Inventor: Joseph Choate Burkett, Addison, TX (US)

( * ) Notice: Subject to any disclaimer, the term of this patent is extended or adjusted under 35 U.S.C. 154(b) by 0 days.

(21) Appl. No.: 17/964,685

(22) Filed: Oct. 12, 2022

(65) Prior Publication Data
US 2023/0173195 A1    Jun. 8, 2023

Related U.S. Application Data

(63) Continuation of application No. 16/570,939, filed on Sep. 13, 2019, now abandoned, which is a continuation of application No. PCT/US2018/022506, filed on Mar. 14, 2018.

(60) Provisional application No. 62/471,168, filed on Mar. 14, 2017.

(51) Int. Cl.
    *A61M 5/42*       (2006.01)
    *A61M 5/30*       (2006.01)
    *A61M 5/32*       (2006.01)

(52) U.S. Cl.
CPC ............... *A61M 5/422* (2013.01); *A61M 5/30* (2013.01); *A61M 5/3202* (2013.01); *A61M 5/3221* (2013.01); *A61M 5/3271* (2013.01); A61M 2205/0211 (2013.01); A61M 2205/3368 (2013.01); A61M 2205/3633 (2013.01); A61M 2205/3673 (2013.01); A61M 2205/582 (2013.01); A61M 2205/609 (2013.01); A61M 2205/8206 (2013.01)

(58) Field of Classification Search
CPC ................ A61M 5/422; A61M 5/3271; A61M 2205/3368; A61M 2205/3673; A61M 5/42; A61M 5/2033
See application file for complete search history.

(56) References Cited

U.S. PATENT DOCUMENTS

| | | |
|---|---|---|
| 5,236,419 A | 8/1993 | Seney |
| 5,300,041 A | 4/1994 | Haber et al. |
| 6,228,067 B1 | 5/2001 | Gabriel |
| 6,290,683 B1 | 9/2001 | Erez et al. |
| 7,981,080 B2 | 7/2011 | Halaka |
| 9,095,660 B2 | 8/2015 | Larsen et al. |

(Continued)

FOREIGN PATENT DOCUMENTS

| | | |
|---|---|---|
| EP | 2591725 A1 | 5/2013 |
| JP | 2005080832 A | 3/2005 |

(Continued)

OTHER PUBLICATIONS

PCT/US2018/022506 International Search Report and Written Opinion dated Jul. 10, 2018.

(Continued)

*Primary Examiner* — Bradley J Osinski
(74) *Attorney, Agent, or Firm* — Wilson Sonsini Goodrich & Rosati

(57) ABSTRACT

A pain-reducing injection apparatus to enhance the safety, efficacy, and efficiency of injection procedures which utilize topical pain-reducing measures. Apparatuses and methods of use provide pain reduction through thermal cooling of an injection region or vibrating the region or both, and optionally include safety shielding and lockout features.

20 Claims, 9 Drawing Sheets

(56) References Cited

U.S. PATENT DOCUMENTS

| | | |
|---|---|---|
| 9,352,100 B2 * | 5/2016 | Ward .................... A61M 5/326 |
| 9,492,355 B2 | 11/2016 | Ratnakar et al. |
| 2008/0086063 A1 | 4/2008 | Baxter et al. |
| 2010/0049126 A1 | 2/2010 | Bronfeld et al. |
| 2010/0174237 A1 | 7/2010 | Halaka |
| 2014/0358084 A1 | 12/2014 | Mcloughlin et al. |
| 2015/0051545 A1 | 2/2015 | Henderson et al. |
| 2016/0279350 A1 | 9/2016 | Besirli et al. |
| 2020/0023144 A1 | 1/2020 | Burkett |

FOREIGN PATENT DOCUMENTS

| | | |
|---|---|---|
| JP | 2015062563 A | 4/2015 |
| JP | 2015510802 A | 4/2015 |
| WO | WO-2013036625 A1 | 3/2013 |
| WO | WO-2016064916 A1 | 4/2016 |
| WO | WO-2018170176 A1 | 9/2018 |

OTHER PUBLICATIONS

U.S. Appl. No. 16/570,939 Office Action dated Apr. 12, 2022.
U.S. Appl. No. 16/570,939 Office Action dated Aug. 3, 2021.

* cited by examiner

PAIN-REDUCING INJECTION APPARATUS

CROSS-REFERENCE

This application is a continuation of U.S. application Ser. No. 16/570,939, filed Sep. 13, 2019, which is a continuation of International Application No. PCT/US2018/022506, filed on Mar. 14, 2018, which claims the benefit of U.S. Provisional Patent Application No. 62/471,168, filed Mar. 14, 2017, both of which are incorporated herein by reference in their entireties.

BACKGROUND

Millions of injections are given each day for an array of reasons including cosmetic procedures, life-saving injections of antibiotics for the acutely ill, and repeated injections for those suffering from chronic diseases such as diabetes. In fact, approximately 1.25 million people in the United States have Type 1 diabetes, which often requires numerous injections each day for both drawing blood and injecting insulin. Of these 1.25 million people, approximately 200,000 are pediatric patients.

Many patients who receive injections have an inherent fear of injections, often attributed to the pain associated with such injections. Such a fear can lead to a patient refusing necessary treatment, which results in further complications. As a result, the medical industry has been working to reduce pain associated with injections as a way of minimizing such a fear.

Pain reduction methods for injections include topical anesthetic medications, skin refrigerant spray, and topical skin-cooling devices. However, all of these methods have issues which deter from more widespread use. First, the use of topical anesthetic medications and skin refrigerant spray has serious side effects; including, without limitation, allergic reactions, skin irritation, permanently freezing skin cells, seizures, arrhythmias, and even death. In addition to the potentially severe side effects, topical anesthetic medications work to chemically block the transmission of impulses through nerves, generally taking a period of time, anywhere from 10 to 30 minutes, to start working. Moreover, topical skin-cooling devices must be stored in a freezer for a period of time before use in order to sufficiently lower the temperature of the device. While topical skin-cooling devices are generally used with fewer side effects, they still present the opportunity for the transmission of blood borne pathogens as the frozen surface of the device is reused among patients.

The most-advanced devices used for pre-injection pain reduction utilize topical cooling and vibration in tandem. However, similar to other topical skin-cooling methods and the potential for the transmission of blood borne pathogens, these devices are substantially limited in the ability to only cool skin within the proximity of needle insertion without the ability to cool the exact location where the needle will be inserted. Such proximity cooling is not as effective as cooling the exact site of needle insertion, which results in little to no reduction in pain.

Accordingly, a need exists for a pain-reducing measure which minimizes the amount of time to cool the skin at the specific needle-insertion site. Additionally, such a pain-reducing measure would ideally minimize or negate the risk for reaction, infection, or transmission of blood borne pathogens by utilizing acceptable sanitation measures within the medical industry. To date, no such medical apparatus exists.

SUMMARY

Disclosed herein, in certain embodiments, are pain-reducing injection apparatuses, comprising: a pen-type injector sleeve comprising: a housing configured to operatively receive a drug delivery device, the housing comprising a distal end comprising a distal wall between an inner surface and an active-cooling surface positioned to contact an injection region of an individual when in use; and a thermoelectric cooling system comprising: a thermoelectric cooler comprising a cooling plate, the thermoelectric cooler mounted against the inner surface of the distal end and configured to cool the active-cooling surface by conduction; and a controller operatively coupled to the thermoelectric cooler. In some embodiments, the drug delivery device is an injector pen. In some embodiments, the drug delivery device is a syringe. In some embodiments, the drug delivery device is a jet injector. In some embodiments, the housing is configured to reversibly receive the drug delivery device. In some embodiments, the housing is configured to permanently receive the drug delivery device. In some embodiments, the cooling plate is composed of a thermally insulated material. In some embodiments, the cooling plate is a ceramic plate. In some embodiments, the controller controls a temperature of the cooling plate. In some embodiments, the thermoelectric cooling system comprises a power source operatively coupled to the thermoelectric cooler and to the controller. In some embodiments, the thermoelectric cooling system comprises a temperature sensor operatively connected to the controller, the thermoelectric cooler, and the active-cooling surface. In some embodiments, the temperature sensor is configured to detect a temperature of the cooling plate and of the active-cooling surface. In some embodiments, the thermoelectric cooling system comprises a heating plate facing away from the inner surface of the distal end. In some embodiments, the heating plate is in thermal connection with a heat sink. In some embodiments, the heat sink absorbs heat emitted by the heating plate. In some embodiments, the thermoelectric cooling system comprises a fan configured to dissipate heat emitted by the heating plate. In some embodiments, the pain reduction apparatus is configured to reversibly receive a needle assembly. In some embodiments, the needle assembly comprises a needle and a needle hub. In some embodiments, the pen-type injector sleeve comprises a needle cap configured to receive a needle assembly. In some embodiments, the pain-reducing injection apparatus comprises a fingerprint authentication locking mechanism comprising a fingerprint sensor and a needle cap lock. In some embodiments, the needle cap lock is unlocked upon recognition of a fingerprint of a user by the fingerprint sensor. In some embodiments, the fingerprint sensor is located on the needle cap. In some embodiments, the power source is a battery. In some embodiments, the battery is rechargeable.

Disclosed herein, in certain embodiments, are pain-reducing injection apparatuses, comprising: a pen-type injector sleeve comprising: a housing configured to operatively receive a drug delivery device, the housing comprising a distal surface located at a distal region of the housing, the distal surface positioned to contact an injection region of an individual when in use; and a vibrator mounted in the housing, the vibrator configured to cause a distal region of the housing to vibrate. In some embodiments, the drug delivery device is an injector pen. In some embodiments, the drug delivery device is a syringe. In some embodiments, the drug delivery device is a jet injector. In some embodiments, the housing is configured to reversibly receive the drug delivery device. In some embodiments, the housing is configured to permanently receive the drug delivery device. In some embodiments, the vibrator is configured to cause the distal surface, the drug delivery device, or a needle to vibrate. In some embodiments, the vibrator comprises a motor. In some embodiments, the motor is an eccentric rotating mass vibration motor or a linear resonant actuator. In some embodiments, the vibrator is operatively coupled to a power source. In some embodiments, the power source is a battery. In some embodiments, the battery is rechargeable. In some embodiments, the pen-type injector sleeve is configured to reversibly receive a needle assembly. In some embodiments, the needle assembly comprises a needle and a needle hub. In some embodiments, the pain-reducing injection apparatus comprises a needle cap configured to receive a needle assembly. In some embodiments, the pain-reducing injection apparatus comprises a fingerprint authentication locking mechanism comprising a fingerprint sensor and a needle cap lock. In some embodiments, the needle cap lock is unlocked upon recognition of a fingerprint of a user by the fingerprint sensor. In some embodiments, the fingerprint sensor is located on the needle cap.

Disclosed herein, in certain embodiments, are pain-reducing injection apparatuses, comprising: a pen-type injector sleeve comprising: a housing configured to operatively receive a drug delivery device, the housing comprising a distal end comprising a distal wall between an inner surface and an active-cooling surface positioned to contact an injection region of an individual when in use; a thermoelectric cooler comprising a cooling plate mounted against the inner surface of the distal end and configured to cool the active-cooling surface by conduction; and a vibrator mounted in the housing, the vibrator configured to cause the distal end of the housing to vibrate.

In some embodiments, the drug delivery device is an injector pen. In some embodiments, the drug delivery device is a syringe. In some embodiments, the drug delivery device is a jet injector. In some embodiments, the housing is configured to reversibly receive the drug delivery device. In some embodiments, the housing is configured to permanently receive the drug delivery device. In some embodiments, the thermoelectric cooler comprises a cooling plate, a heating plate, a controller, a power source, and a temperature sensor. In some embodiments, the cooling plate and the heating plate are composed of a thermally insulating material. In some embodiments, the cooling plate is a ceramic plate. In some embodiments, the controller controls a temperature of the cooling plate. In some embodiments, the temperature sensor is operatively coupled to the cooling plate, to the heating plate, and to the active-cooling surface. In some embodiments, the temperature sensor detects a temperature of the cooling plate. In some embodiments, the temperature sensor detects a temperature of the active-cooling surface. In some embodiments, the power source is operatively connected to the thermoelectric cooler, to the controller, and to the temperature sensor. In some embodiments, the power source is a battery. In some embodiments, the battery is rechargeable. In some embodiments, the active-cooling surface is a thermally conductive surface. In some embodiments, the vibrator is configured to cause the active-cooling surface, the drug delivery device, and/or a needle to vibrate. In some embodiments, the vibrator comprises a motor. In some embodiments, the motor is an eccentric rotating mass vibration motor or a linear resonant actuator. In some embodiments, the pain reduction apparatus is configured to reversibly receive a needle assembly. In some embodiments, the needle assembly comprises a needle and a needle hub. In some embodiments, the pain-reducing injection apparatus comprises a needle cap. In some embodiments, the pain reduction apparatus comprises a fingerprint authentication locking mechanism comprising a fingerprint sensor and a needle cap lock. In some embodiments, the needle cap lock is unlocked upon recognition of a fingerprint of a user by the fingerprint sensor. In some embodiments, the fingerprint sensor is located on the needle cap.

Disclosed herein, in certain embodiments, are pain-reducing injection apparatuses, comprising: a pen-type injector sleeve comprising: a housing configured to operatively receive a drug delivery device, the housing comprising a distal surface located at a distal region of the housing, the distal surface configured to contact an injection region of an individual when in use; and a needle assembly comprising: a needle, an outer sleeve having a first inner surface comprising a ramped track, and a first outer surface, an inner sleeve positioned within the outer sleeve, the inner sleeve comprising: a second inner surface, a second outer surface facing the first inner surface, an aperture comprising a perimeter and a perimeter wall extending between the second inner surface and the second outer surface along the perimeter, and a distal needle insertion shield coaxially aligned with the inner sleeve and with the outer sleeve, the distal needle insertion shield comprising a distal shield insertion arm configured to travel along the perimeter of the aperture in contact with the perimeter wall of the aperture as the distal needle insertion shield rotates about its axis, and wherein the distal shield insertion arm extends through the aperture and is configured to travel within and along the ramped track as the distal needle insertion shield is axially rotated about the axis.

In some embodiments, the drug delivery device is an injector pen. In some embodiments, the drug delivery device is a syringe. In some embodiments, the drug delivery device is a jet injector. In some embodiments, the housing is configured to reversibly receive the drug delivery device. In some embodiments, the drug delivery device is reversibly screwed into the housing. In some embodiments, the drug delivery device is reversibly snapped onto the housing. In some embodiments, the housing is configured to permanently receive the drug delivery device. In some embodiments, the pain-reducing injection apparatus comprises a vibrator. In some embodiments, the vibrator comprises a motor. In some embodiments, the motor is an eccentric rotating mass vibration motor or a linear resonant actuator. In some embodiments, the vibrator is mounted in the housing. In some embodiments, the vibrator is configured to cause the distal region of the housing and/or the needle assembly to vibrate. In some embodiments, the vibrator is configured to cause the distal surface, the drug delivery device, or the needle to vibrate. In some embodiments, the pain-reducing injection apparatus comprises a thermoelectric cooler. In some embodiments, the thermoelectric cooler comprises a cooling plate, a heating plate, a controller, a power source, and a temperature sensor. In some embodiments, the cooling plate and the heating plate are composed of a thermally insulating material. In some embodiments, the cooling plate is a ceramic plate. In some embodiments, the controller controls a temperature of the cooling plate. In some embodiments, the temperature sensor is operatively coupled to the cooling plate, to the heating plate, and to the distal surface. In some embodiments, the temperature sensor detects a temperature of the cooling plate. In some embodiments, the temperature sensor detects a temperature of the distal surface. In some embodiments, the power source is operatively connected to the thermoelectric cooler, to the controller, and to the temperature sensor. In some embodiments, the power source is a battery. In some embodiments, the battery is rechargeable. In some embodiments, the distal surface is a thermally conductive surface. In some embodiments, In some embodiments, the pain-reducing injection apparatus comprises a thermoelectric cooler and a vibrator. In some embodiments, the pain reduction apparatus comprises a needle cap configured to receive the needle assembly. In some embodiments, the pain reduction apparatus comprises a fingerprint authentication locking mechanism comprising a fingerprint sensor and a needle cap lock. In some embodiments, the needle cap lock is unlocked upon recognition of a fingerprint of a user by the fingerprint sensor. In some embodiments, the fingerprint sensor is located on the needle cap. In some embodiments, the ramped track has a start and a finish and a bump positioned medially therebetween. In some embodiments, the distal shield insertion arm travels from the start of the ramped track to the finish of the ramped track as the distal needle insertion shield is axially rotated about the axis. In some embodiments, the bump prevents the distal shield insertion arm to travel from the finish to the start of the ramped track once the distal shield insertion arm overcomes the bump. In some embodiments, deployment of the needle from the needle assembly causes the distal shield insertion arm to overcome the bump and subsequently rest within the track. In some embodiments, the ramped track has a track locking notch positioned at the finish of the ramped track. In some embodiments, the track locking notch is configured to lock the distal shield insertion arm in place after the needle is deployed and retracted. In some embodiments, the ramped track is angled. In some embodiments, the ramped track is angled at an angle of about 45 degrees with respect to the distal surface of the housing. In some embodiments, the aperture has a first end of the aperture and a second end of the aperture. In some embodiments, the first end of the aperture aligns with the start of the ramped track and the second end of the aperture aligns with the finish of the ramped track prior to deployment of the needle. In some embodiments, the perimeter of the aperture has an aperture locking notch positioned at the second end of the aperture. In some embodiments, the perimeter of the aperture has a sloped region originating from the first end of the aperture and ending at a vertical region of the aperture. In some embodiments, the vertical region of the aperture originates from a peak of the sloped region and ends at the aperture locking notch. In some embodiments, the deployment of the needle causes the distal shield insertion arm to rest at the peak of the sloped region, on the perimeter of the aperture. In some embodiments, the aperture locking notch is configured to lock the distal shield insertion arm in place after the needle is deployed and retracted. In some embodiments, the distal shield insertion arm travels from the first end of the aperture to the second end of the aperture as the distal needle insertion shield is axially rotated about the axis. In some embodiments, the distal shield insertion arm is resting on the perimeter of the aperture at the first end of the aperture and within the ramped track at start of the ramped track prior to deployment of the needle. In some embodiments, the outer sleeve is cylindrical. In some embodiments, the inner sleeve is cylindrical. In some embodiments, the outer sleeve is coaxially aligned with the inner sleeve. In some embodiments, the aperture locking notch is aligned with the track locking notch. In some embodiments, the needle is contained within the inner sleeve prior to deployment. In some embodiments, the ramped track is unidirectional. In some embodiments, the distal shield insertion arm is moved distally as the as the distal needle insertion shield is axially rotated about the axis.

Disclosed herein, in certain embodiments, are needle assemblies, comprising: a needle; an outer sleeve having a first inner surface comprising a ramped track, and a first outer surface; an inner sleeve positioned within the outer sleeve, the inner sleeve comprising: a second inner surface, a second outer surface facing the first inner surface, and an aperture comprising a perimeter and a perimeter wall extending between the second inner surface and the second outer surface along the perimeter; and a distal needle insertion shield coaxially aligned with the inner sleeve and with the outer sleeve, the distal needle insertion shield comprising a distal shield insertion arm configured to travel along the perimeter of the aperture in contact with the perimeter wall of the aperture as the distal needle insertion shield rotates about its axis, and wherein the distal shield insertion arm extends through the aperture and is configured to travel within and along the ramped track as the distal needle insertion shield is axially rotated about the axis. In some embodiments, the needle assembly reversibly attaches to a pen injector. In some embodiments, the needle assembly permanently attaches to a pen injector. In some embodiments, the needle assembly is screwed into a pen injector. In some embodiments, the needle assembly is snapped onto a pen injector. In some embodiments, the needle assembly comprises a needle cap configured to receive the needle assembly. In some embodiments, the needle assembly comprises a fingerprint authentication locking mechanism comprising a fingerprint sensor and a needle cap lock. In some embodiments, the needle cap lock is unlocked upon recognition of a fingerprint of a user by the fingerprint sensor. In some embodiments, the fingerprint sensor is located on the needle cap. In some embodiments, the ramped track has a start and a finish and a bump positioned medially therebetween. In some embodiments, the distal shield insertion arm travels from the start of the ramped track to the finish of the ramped track as the distal needle insertion shield is axially rotated about the axis. In some embodiments, the bump prevents the distal shield insertion arm to travel from the finish to the start of the ramped track once the distal shield insertion arm overcomes the bump. In some embodiments, deployment of the needle from the needle assembly causes the distal shield insertion arm to overcome the bump and subsequently rest within the track. In some embodiments, the ramped track has a track locking notch positioned at the finish of the ramped track. In some embodiments, the track locking notch is configured to lock the distal shield insertion arm in place after the needle is deployed and retracted. In some embodiments, the ramped track is angled. In some embodiments, the ramped track is angled at an angle of about 45 degrees with respect to the distal surface of the housing. In some embodiments, the aperture has a first end of the aperture and a second end of the aperture. In some embodiments, the first end of the aperture aligns with the start of the ramped track and the second end of the aperture aligns with the finish of the ramped track prior to deployment of the needle. In some embodiments, the perimeter of the aperture has an aperture locking notch positioned at the second end of the aperture. In some embodiments, the perimeter of the aperture has a sloped region originating from the first end of the aperture and ending at a vertical region of the aperture. In some embodiments, the vertical region of the aperture originates from a peak of the sloped region and ends at the aperture locking notch. In some embodiments, the deployment of the needle causes the distal shield insertion arm to rest at the peak of the sloped region, on the perimeter of the aperture. In some embodiments, the aperture locking notch is configured to lock the distal shield insertion arm in place after the needle is deployed and retracted. In some embodiments, the distal shield insertion arm travels from the first end of the aperture to the second end of the aperture as the distal needle insertion shield is axially rotated about the axis. In some embodiments, the distal shield insertion arm is resting on the perimeter of the aperture at the first end of the aperture and within the ramped track at start of the ramped track prior to deployment of the needle. In some embodiments, the outer sleeve is cylindrical. In some embodiments, the inner sleeve is cylindrical. In some embodiments, the outer sleeve is coaxially aligned with the inner sleeve. In some embodiments, the aperture locking notch is aligned with the track locking notch. In some embodiments, the needle is contained within the inner sleeve prior to deployment. In some embodiments, the ramped track is unidirectional. In some embodiments, the distal shield insertion arm is moved distally as the as the distal needle insertion shield is axially rotated about the axis.

Disclosed herein, in certain embodiments, are needle caps, comprising: a housing, the housing configured to receive a needle assembly; and a fingerprint authentication locking mechanism for selectively engaging and disengaging the needle cap from the needle assembly; wherein the fingerprint authentication locking mechanism comprises a fingerprint sensor and a needle cap lock. The In some embodiments, the fingerprint sensor is located on the needle cap. In some embodiments, the needle cap lock is unlocked upon recognition of a fingerprint of a user by the fingerprint sensor. In some embodiments, the needle cap comprises a power source operatively coupled to the fingerprint sensor and needle cap lock. In some embodiments, the power source is a battery. In some embodiments, the battery is rechargeable. In some embodiments, the needle cap is configured to operatively receive a distal end of a pen-type injector.

Disclosed herein, in certain embodiments, are methods of using the pain-reducing apparatuses provided herein, comprising: obtaining the pain-reducing injection apparatus with a drug delivery device loaded therein, cooling the active-cooling surface using the thermoelectric cooling system, contacting the injection region with the active-cooling surface of the pain-reducing injection apparatus, inserting a needle of the drug delivery device into the injection region, and delivering a medicament into the injection region of the individual. In some embodiments, the active-cooling surface is cooled to a temperature ranging between about −10 degrees C. to about 10 degrees C. In some embodiments, the injection region is contacted with the active-cooling surface for about 1 minute to about 5 minutes prior to insertion of the needle.

Disclosed herein, in certain embodiments, are methods of using the pain-reducing apparatuses provided herein, comprising: obtaining the pain-reducing injection apparatus with a drug delivery device loaded therein, activating a vibration using the vibrator, contacting the injection region with the distal surface of the pain-reducing injection apparatus, inserting a needle of the drug delivery device into the injection region, and delivering a medicament into the injection region of the individual. In some embodiments, the distal surface is vibrating when the needle is inserted into the injection region of the individual. In some embodiments, the needle is vibrating when the needle is inserted into the injection region of the individual. In some embodiments, the vibration has a vibration frequency ranging from about 100 Hz to about 300 Hz. In some embodiments, the vibration has an amplitude ranging from about 0.3 G to about 125 G.

Disclosed herein, in certain embodiments, are methods of using the pain-reducing apparatuses provided herein, comprising: obtaining the pain-reducing injection apparatus with a drug delivery device loaded therein, cooling the active-cooling surface using the thermoelectric cooler, activating a vibration using the vibrator, contacting the injection region with the active-cooling surface of the pain-reducing injection apparatus, inserting a needle of the drug delivery device into the injection region, and delivering a medicament into the injection region of the individual. In some embodiments, the active-cooling surface is cooled to a temperature ranging between about −10 degrees C. to about 10 degrees C. In some embodiments, the injection region is contacted with the active-cooling surface for about 1 minute to about 5 minutes prior to insertion of the needle. In some embodiments, the active-cooling surface is vibrating when the needle is inserted into the injection region of the individual. In some embodiments, the needle is vibrating when the needle is inserted into the injection region of the individual. In some embodiments, the vibration has a vibration frequency ranging from about 100 Hz to about 300 Hz. In some embodiments, the vibration has an amplitude ranging from about 0.3 G to about 125 G.

Disclosed herein, in certain embodiments, are methods of using the pain-reducing apparatuses, comprising: obtaining the pain-reducing injection apparatus with a drug delivery device loaded therein, applying a force distally on the drug delivery device, the force translating distally onto the outer sleeve and the inner sleeve causing the needle to be deployed, inserting the needle into the injection region, and delivering a medicament into the injection region of the individual. In some embodiments, applying the force distally on the drug delivery device causes an axial rotation of the distal needle insertion shield about the axis. In some embodiments, applying the force distally on the drug delivery device causes the distal shield insertion arm to travel through the aperture and along the track. In some embodiments, applying the force distally on the drug delivery device causes the distal shield insertion arm to travel from the first end of the aperture and the start of the ramped track to the second end of the aperture and finish of the ramped track. In some embodiments, the needle is retracted into the inner sleeve when a user stops applying the force distally on the drug delivery.

Disclosed herein, in certain embodiments, are methods comprising delivering or providing a device disclosed herein.

Disclosed herein, in certain embodiments, are methods of activating cooling or activating vibration in a pain-reducing injection apparatuses provided herein, comprising cooling a surface of the device using a thermoelectric cooler, activating vibration in the device using a vibrator, loading a drug delivery device into the pain-reducing injection apparatus, and loading a needle assembly into the pain-reducing injection apparatus.

Disclosed herein, in certain embodiments, are methods comprising delivering or providing a needle assembly described herein.

Disclosed herein, in certain embodiments, are methods of activating cooling or activating vibration in a needle assembly provided herein, comprising cooling a surface of the device using a thermoelectric cooler, activating vibration in the device using a vibrator, and loading the needle assembly into a pain-reducing injection apparatus or a pen injector.

In accordance with the present disclosure, the safety and effectiveness of topical pain-reducing measures is enhanced through the utilization of a handheld, electrothermal apparatus (hereinafter, "pain-reducing injection apparatus") capable of both administering localized pain-reducing measures and injecting a hypodermic needle. Additionally, in some embodiments, interchangeable, disposable needles and a skin surface barrier are utilized to prevent the transmission of dangerous pathogens. Such an apparatus provides a safer method to minimize pain by applying the pain-reducing measures directly to the site of needle insertion and decreasing or eliminating the time between the administration of the pain-reducing measure and the insertion of a hypodermic needle.

In some embodiments, the pain-reducing injection apparatus features pain-reducing measures; including, without limitation, a thermoelectric cooling unit, a vibrating unit, and other non-invasive components. In some embodiments, such components are to be used in accord or as alternatives of each other. In some embodiments, such pain-reducing measures are manually activated by a control on the exterior of the apparatus.

In some embodiments, the tip of the pain-reducing injection apparatus features a replaceable cap and/or a needle assembly comprised of a retractable hypodermic needle. Such a configuration allows for a safe, disease-free injection at the point of maximum pain reduction due to the sterilized nature of each replaceable needle assembly at the tip of the pain-reducing injection pin.

In some embodiments, the pain-reducing injection apparatus also features options for the administration of medication through the replaceable hypodermic needle. In certain embodiments, the pain-reducing injection apparatus features an additional attachment to hold a vial of medication. In some embodiments, the medication attachment is replaceable and adjustable to allow for the administration of a variety of medication and dosage amounts. In addition to the medication attachment, in certain embodiments, the pain-reducing injection apparatus attaches directly to a syringe for the administration of medication.

Aside from the common materials used to create hypodermic needles and electrothermal, vibrating, or other pain-reducing components, the pain-reducing injection apparatus is made of any desired material. However, certain embodiments of the pain-reducing injection apparatus advantageously utilize materials which offer the highest strength-to-weight ratio while also providing for optimal thermodynamic transfer between the injection apparatus and a patient's skin.

The above as well as additional features and advantages of the present invention will become apparent in the following written detailed description.

BRIEF DESCRIPTION OF THE DRAWINGS

The novel features of the subject matter disclosed herein are set forth with particularity in the appended claims. A better understanding of the features and advantages of the subject matter disclosed herein will be obtained by reference to the following detailed description that sets forth illustrative embodiments, in which the principles of the subject matter disclosed herein are utilized, and the accompanying drawings of which:

FIG. 2A illustrates an example of the pain-reducing injection apparatus comprising a sleeve, an injector, and a needle assembly. FIG. 2B illustrates an example of the pain-reducing injection apparatus comprising a sleeve, an injector, and a needle assembly; the needle assembly is shown with an exposed needle.

FIG. 3A illustrates the needle assembly at its initial position. FIG. 3B illustrates the needle assembly after initiating deployment of the needle. FIG. 3C illustrates the needle assembly once the needle has been exposed. FIG. 3D illustrates the needle assembly at its final, retracted position.

DETAILED DESCRIPTION

Figure 1:
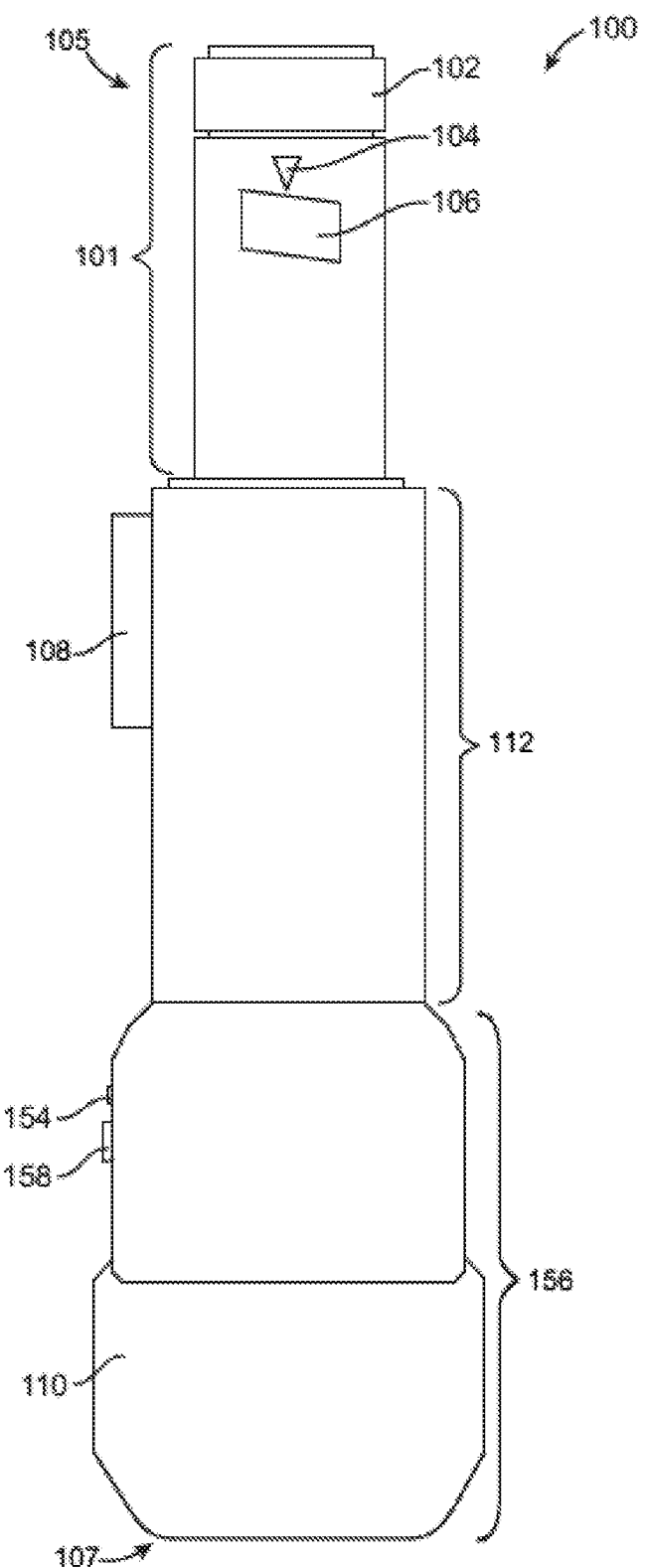
FIG. 1 depicts a front view of a pain-reducing injection apparatus comprising a sleeve, an injector, and a cap.

While preferred embodiments of the subject matter disclosed herein have been shown and described herein, it will be obvious to those skilled in the art that such embodiments are provided by way of example only. Numerous variations, changes, and substitutions will now occur to those skilled in the art without departing from the subject matter disclosed herein. It should be understood that various alternatives to the embodiments of the subject matter disclosed herein may be employed in practicing the subject matter disclosed herein. It is intended that the following claims define the scope of the subject matter disclosed herein and that methods and structures within the scope of these claims and their equivalents be covered thereby.

Definitions

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The term "about" or "approximately" refers to an amount that is near the stated amount by about 10%, 5%, or 1%, including increments therein. For example, "about" or "approximately" can mean a range including the particular value and ranging from 10% below that particular value and spanning to 10% above that particular value.

The terms "subject," "individual," "user," and "patient" are used interchangeably herein to refer to a vertebrate, for example, a mammal. Mammals include, but are not limited to, murine, simians, humans, farm animals, sport animals, and pets. In some instances, the terms "user" and "patient" are used interchangeably; for example, when the "patient"

utilizes the pain-reducing injection apparatuses described herein. Designation as a "subject," "individual," "user," or "patient" does not necessarily entail supervision of a medical professional.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the term "injection region" is defined as the area of skin or tissue of an individual that is adjacent to or proximal to an injection site where a needle or a jet of an injection liquid enters or penetrates the skin or tissue of the individual.

Pain-Reducing Injection Apparatus

In some embodiments provided herein, are pain-reducing injection apparatuses that feature a thermoelectric cooling function, a vibration function, or a combination of both a thermoelectric cooling and a vibration function. In some embodiments, mechanical vibration and cooling of a skin surface near or at an injection site (i.e., the point where a needle penetrates the skin of a patient) decreases pain and anxiety significantly compared to the normal injection procedures that do not have the capability to use cooling and/or vibration features.

In addition, in some embodiments, provided herein, are replaceable needle caps that comprise a needle cap lock mechanism further comprising a fingerprint sensor. The Center for Disease Control (CDC) and the Federal Drug Administration (FDA) have raised concern regarding the transmission of viruses, bloodborne pathogens, etc. from shared used of injector pens. For example, bloodborne pathogen transmission due to multi-patient sharing of insulin injectors is a common issue for hospitals. In some embodiments, needle caps that can be securely engaged and disengaged via recognition of a fingerprint of a patient, such as those provided herein, prevent the use of accidental and/or unwanted sharing of needles, syringes, and/or injectors.

Disclosed herein, in certain embodiments, are pain-reducing injection apparatuses, comprising: a pen-type injector sleeve comprising: a housing configured to operatively receive a drug delivery device, the housing comprising a distal end comprising a distal wall between an inner surface and an active-cooling surface positioned to contact an injection region of an individual when in use; and a thermoelectric cooling system comprising: a thermoelectric cooler comprising a cooling plate, the thermoelectric cooler mounted against the inner surface of the distal end and configured to cool the active-cooling surface by conduction; and a controller operatively coupled to the thermoelectric cooler.

Further disclosed herein, in certain embodiments, are pain-reducing injection apparatuses, comprising: a pen-type injector sleeve comprising: a housing configured to operatively receive a drug delivery device, the housing comprising a distal surface located at a distal region of the housing, the distal surface positioned to contact an injection region of an individual when in use; and a vibrator mounted in the housing, the vibrator configured to cause a distal region of the housing to vibrate.

Additionally disclosed herein, in certain embodiments, are pain-reducing injection apparatuses, comprising: a pen-type injector sleeve comprising: a housing configured to operatively receive a drug delivery device, the housing comprising a distal surface located at a distal region of the housing, the distal surface configured to contact an injection region of an individual when in use; and a needle assembly comprising: a needle, an outer sleeve having a first inner surface comprising a ramped track, and a first outer surface, an inner sleeve positioned within the outer sleeve, the inner sleeve comprising: a second inner surface, a second outer surface facing the first inner surface, an aperture comprising a perimeter and a perimeter wall extending between the second inner surface and the second outer surface along the perimeter, and a distal needle insertion shield coaxially aligned with the inner sleeve and with the outer sleeve, the distal needle insertion shield comprising a distal shield insertion arm configured to travel along the perimeter of the aperture in contact with the perimeter wall of the aperture as the distal needle insertion shield rotates about its axis, and wherein the distal shield insertion arm extends through the aperture and is configured to travel within and along the ramped track as the distal needle insertion shield is axially rotated about the axis.

Further disclosed herein, in certain embodiments, are needle assemblies, comprising: a needle; an outer sleeve having a first inner surface comprising a ramped track, and a first outer surface; an inner sleeve positioned within the outer sleeve, the inner sleeve comprising: a second inner surface, a second outer surface facing the first inner surface, and an aperture comprising a perimeter and a perimeter wall extending between the second inner surface and the second outer surface along the perimeter; and a distal needle insertion shield coaxially aligned with the inner sleeve and with the outer sleeve, the distal needle insertion shield comprising a distal shield insertion arm configured to travel along the perimeter of the aperture in contact with the perimeter wall of the aperture as the distal needle insertion shield rotates about its axis, and wherein the distal shield insertion arm extends through the aperture and is configured to travel within and along the ramped track as the distal needle insertion shield is axially rotated about the axis.

Additionally disclosed herein, in certain embodiments, are needle caps, comprising: a housing, the housing configured to receive a needle assembly; and a fingerprint authentication locking mechanism for selectively engaging and disengaging the needle cap from the needle assembly; wherein the fingerprint authentication locking mechanism comprises a fingerprint sensor and a needle cap lock.

Further disclosed herein, in certain embodiments, are methods of using a pain-reducing apparatus, comprising: obtaining the pain-reducing injection apparatus with a drug delivery device loaded therein, cooling the active-cooling surface using the thermoelectric cooling system, contacting the injection region with the active-cooling surface of the pain-reducing injection apparatus, inserting a needle of the drug delivery device into the injection region, and delivering a medicament into the injection region of the individual.

Disclosed herein, in certain embodiments, are methods of using a pain-reducing apparatus, comprising: obtaining the pain-reducing injection apparatus with a drug delivery device loaded therein, activating a vibration using the vibrator, contacting the injection region with the distal surface of the pain-reducing injection apparatus, inserting a needle of the drug delivery device into the injection region, and delivering a medicament into the injection region of the individual.

Additionally disclosed herein, in certain embodiments, are methods of using a pain-reducing apparatus, comprising: obtaining the pain-reducing injection apparatus with a drug delivery device loaded therein, cooling the active-cooling surface using the thermoelectric cooler, activating a vibration using the vibrator, contacting the injection region with the active-cooling surface of the pain-reducing injection apparatus, inserting a needle of the drug delivery device into the injection region, and delivering a medicament into the injection region of the individual.

Further disclosed herein, in certain embodiments, are methods of using a pain-reducing apparatus, comprising: obtaining the pain-reducing injection apparatus with a drug delivery device loaded therein, applying a force distally on the drug delivery device, the force translating distally onto the outer sleeve and the inner sleeve causing the needle to be deployed, inserting the needle into the injection region, and delivering a medicament into the injection region of the individual.

Disclosed herein, in certain embodiments, are methods comprising delivering or providing a pain-reducing injection apparatus. Additionally disclosed herein, in certain embodiments, are methods of activating cooling or activating vibration in a pain-reducing injection apparatus, comprising cooling a surface of the device using a thermoelectric cooler, activating vibration in the device using a vibrator, loading a drug delivery device into the pain-reducing injection apparatus, and loading a needle assembly into the pain-reducing injection apparatus.

Disclosed herein, in certain embodiments, are methods comprising delivering or providing a needle assembly. Further disclosed herein, in certain embodiments, are methods of activating cooling or activating vibration in a needle assembly, comprising cooling a surface of the device using a thermoelectric cooler, activating vibration in the device using a vibrator, and loading the needle assembly into a pain-reducing injection apparatus or a pen injector.

As noted above, current measures utilized to reduce pain prior to the insertion of a needle into a patient's skin are lacking in disease prevention, speed or ease of use, location-accurate pain reduction, convenience, or any combination of the above. Currently, no known apparatus exists to remedy the problems associated with known pain-reducing measures.

Provided herein is a pain-reducing injection apparatus which provides fast, accurate, and sterilized pain reduction capable of also inserting a needle into the patient's skin at the spot of pain reduction. In an embodiment provided herein, the pain-reducing injection apparatus is generally comprised of the body of the pain-reducing injection apparatus and a replaceable cap or cartridge that is secured and removed from the end of the pain-reducing injection apparatus. In some embodiments, the body of the injection apparatus houses a vial-containing medication or other fluid. In some embodiments, the body of the injection apparatus is configured to attach directly to a standard syringe. In some embodiments, the needle assembly is generally comprised of a hypodermic needle enclosed within a cylindrical, center shaft at the distal tip of the injection apparatus.

FIG. 1 shows an injection apparatus with a cap 110 secured. In some embodiments, the pain-reducing measures of the apparatus are located at the very tip of a tube protruding from the distal end of the injection apparatus. In some embodiments, the replaceable needle assembly with the cylindrical shaft is uniquely designed to interconnect with the distal end of the injection apparatus, as the cylindrical shaft (and enclosed needle) fits within the interior of the of the tube protruding from the distal end of the injection apparatus while also encapsulating the exterior of the distal end of the injection apparatus. The unique design allows for the injection site and pain-reducing measures to be located on the same plane and centered on the same axis.

In some embodiments provided herein, when the needle assembly is secured to the body of the pain-reducing injection apparatus, the cylindrical shaft, with the hypodermic needle enclosed, is secured to a vial or syringe containing medication or other fluid. In some embodiments, a user then places the end of the needle assembly attached to the pain-reducing injection apparatus in contact with the patient, such that the body of the device is perpendicular to the surface of the patient's skin: only the distal, external surface of the needle assembly contacts the patient's skin. In some embodiments, a user then activates the pain-reducing component of the apparatus via a manual control located on the exterior of the body of the apparatus.

In an embodiment utilizing a cooling pain-reducing component, an activated thermoelectric cooler located at the distal end of the apparatus allows for heat to transfer from the patient's skin, through the surface of the needle assembly, and into the thermoelectric cooler, thereby locally reducing the temperature and pain sensation in the skin while not overcooling the skin within a matter of seconds. In some embodiments, once the skin has cooled to a desired temperature, the apparatus notifies the user through a light, sound, or other notifying means. Although a thermoelectric cooler is described herein, in some embodiments, other pain-reduction means incorporate vibration or any other non-invasive pain-reduction method either as an alternative or in combination.

In some embodiments, after the pain-reduction method has been utilized to a satisfactory degree, a user then depresses a manual control on the exterior of the body of the apparatus to activate the insertion of the needle and/or delivery of the injection. In some embodiments, once the injection is completed, the device automatically retracts the needle and shuts down the pain-reducing component of the apparatus. In some embodiments, the removable cap is then removed and discarded by the user.

In some embodiments provided herein, the manual control for injection is located at the proximal end of the apparatus. In some embodiments, such a manual control for injection also contains a dial or other controller for selecting a desired dosage amount for injection.

In yet other certain embodiments of the present, the apparatus is designed to attach directly to a standard syringe. In such an embodiment, a user first secures a needle assembly to the distal end of the apparatus as described above. In some embodiments, the user then inserts a standard syringe into the apparatus, whereby the needle within the needle assembly penetrates the syringe to prepare for the administration of medication. In some embodiments, as described above, a manual control on the exterior of the body of the apparatus initiates the pain-reducing component, which then is followed by the advancement of the needle and injection of medication. In some embodiments, once finished, the cap is then discarded. In some embodiments, the injector or syringe has no needle when placed in the pain-reducing apparatus; in such case, either the needle assembly described herein is attached thereto, or a standard pen needle is attached thereto. In some embodiments, an injector having a syringe and needle pre-attached thereto is used in the pain-reducing apparatus.

Referring to FIG. 1, the pain-reducing injection apparatus attaches to a standard syringe or an injector. In some embodiments, FIG. 1 illustrates a front view of a pain-reducing injection apparatus 100 operatively receiving an injector 101. In some embodiments, the injector 101 is a standard repeating injector. In some embodiments, the injector 101 is a pen-style injector or an injector pen. In some embodiments, the injector 101 is a reusable injector pen, a disposable injector pen, a wearable autoinjector, or a hand-held autoinjector. In some embodiments, the injector or syringe has no needle when placed in the pain-reducing apparatus; in such case, either the needle assembly described herein is attached thereto, or a standard pen needle is attached thereto. In some embodiments, an injector having a syringe and needle pre-attached thereto is used in the pain-reducing apparatus.

In some embodiments, the injector 101 delivers a drug. Non-limiting examples of the drug the injector 101 delivers are: an antibody, a hormone, a small molecule drug, a cytokine, a protein, an antibiotic, an anti-inflammatory, an analgesic, a psychoactive drug, or an anticoagulant. In some embodiments, the antibody is adalimumab. In some embodiments, the hormone is insulin or epinephrine. In some embodiments, the small molecule drug is a drug for the treatment of diabetes. In some embodiments, the small molecule drug is a glucagon-like peptide-1 receptor agonist (GLP-1). In some embodiments, the small molecule drug is a drug that is used for first aid against a chemical warfare agent. In some embodiments, the small molecule drug is a nerve agent antidote. In some embodiments, the psychoactive drug is a benzodiazepine compound, such as but not limited to diazepam, chlordiazepoxide, temazepam, midazolam, and clonazepam. In some embodiments, the cytokine is interferon-β1a or erythropoietin. In some embodiments, the protein is a fusion protein such as but not limited to etanercept. In some embodiments, the anticoagulant is enoxaparin.

In some embodiments, the injector 101 comprises a cartridge containing a drug (not shown in FIG. 1). In some embodiments, the injector 101 comprises a dial 102 that adjusts a unit dose of a drug. In some embodiments, the user rotates the dial 102 clockwise to increase the unit dose of a drug. In some embodiments, the user rotates the dial 102 counterclockwise to increase the unit dose of a drug. In some embodiments, the injector 101 comprises a unit dose indicator 104. In some embodiments, the injector 101 comprises a unit dose display 106. In some embodiments, the unit dose display 106 displays a unit dose number or a unit dose marker selected by a user. In some embodiments, the unit dose indicator 104 assists the user in aligning a unit dose number or a unit dose marker with the unit dose indicator 104. In some embodiments, the unit dose indicator 104 is a line, a triangle, a light such as a light emitting diode (LED), or a notch. In some embodiments, the injector 101 makes a clicking sound to indicate an increment in a dose unit of a drug as the user rotates the dial 102 clockwise or counterclockwise.

In some embodiments, the pain-reducing injection apparatus 100 comprises an upper body 112 and a lower body 156. In some embodiments, the pain-reducing injection apparatus 100 is configured to hold an injector 101. In some embodiments, the pain-reducing injection apparatus 100 is configured to hold a syringe (not shown in FIG. 1). In some embodiments, the upper body 112 and the lower body 156 are shaped in the form of a "U" which allows the pain-reducing injection apparatus 100 to reversibly hold the cylindrical body of an injector 101 or a syringe for its retention and or release. In some embodiments, the "U"-shaped upper body 112 and the "U"-shaped lower body 156 have a first lateral wall and a second lateral wall opposite from one another and with a curved profile that defines the "U" shape, in a way that accommodates the cylindrical body of the injector 101 or the cylindrical body of a syringe (not shown in FIG. 1). In some embodiments, an injector 101 or a syringe is reversibly attached to the pain-reducing injection apparatus 100 via a snap-on mechanism. In some embodiments, the upper body 112 and/or the lower body 156 comprises at least one projection or groove that reversibly secure the injector 101 into the upper body 112 and/or into the lower body 156. In some embodiments, the projection is a grip, a recess, a lip, or a ring.

In some embodiments, the user inserts the injector 101 into the upper body 112 and/or lower body 156 by pushing the injector 101 into at least one projection, with a light force so that the body of the injector 101 overcomes the projections. In some embodiments, the user releases the injector 101, by pulling on its proximal end 105, with a light force so that the body of the injector 101 passes the projections. In some embodiments, alternatively, the user releases the injector 101, by sliding the injector 101 along the upper body 112 and/or lower body 156, towards the proximal end 105. In some embodiments, the upper body 112 and/or lower body 156 are composed of a soft, flexible material in order to enable separation of the first lateral wall of the "U" and second lateral wall of the "U" when the injector 101 is either inserted or released. In some embodiments, the upper body 112 and/or lower body 156 are composed of a rigid material. In some embodiments, the projection is composed of a soft, flexible material in order to enable its separation when the injector 101 is either inserted or released.

In some embodiments, a needle cap 110 is attached to the distal end 107 of the lower body of the device 156 in its lateral aspects and is attached to the distal end of the injector 101 in its medial aspects, as shown in FIG. 1. In some embodiments, the upper body 112 has an insertion activation button 108 which is depressed by a user to allow the insertion of a needle into the tissue of a patient. FIG. 1 further shows the lower body 156 comprising a light indicator 154 and a thermoelectric cooling and vibration activator button 158. In some embodiments, the light indicator 154 turns on when a user activates the thermoelectric cooling function of the device and/or the vibration function of the device. In some embodiments, the light indicator 154 is a light-emitting diode (LED). In some embodiments, the light indicator 154 will flash until the thermoelectric cooling function has reached a desired temperature. In some embodiments, the light indicator 154 comprises a first LED of a first color and a second LED of a second color. In some embodiments, the first LED turns on when the thermoelectric function is activated and the second LED turns on when the vibration function is activated.

Figure 2A:
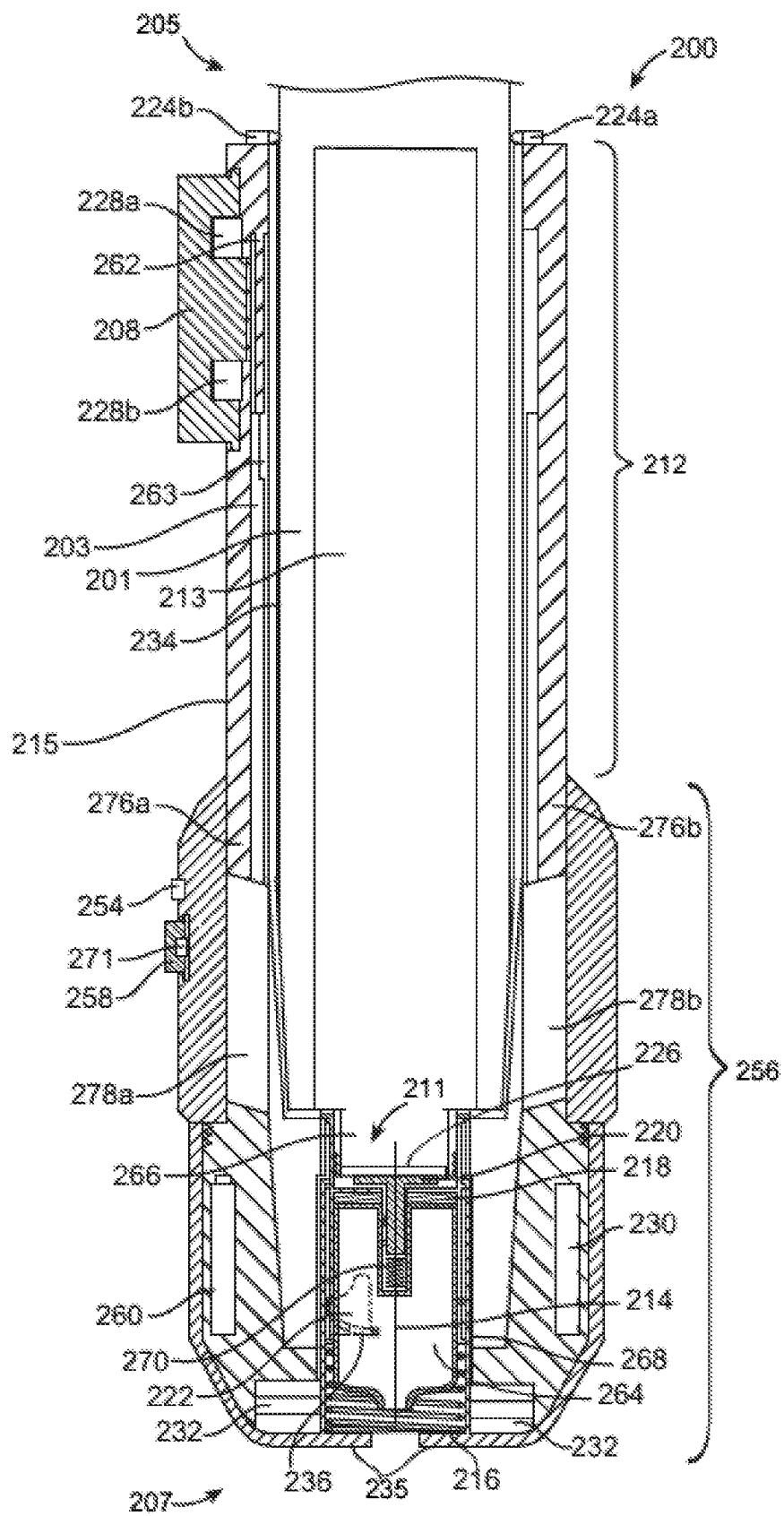
FIGS. 2A and 2B depict an embodiment of a pain-reducing injection.
Figure 2B:
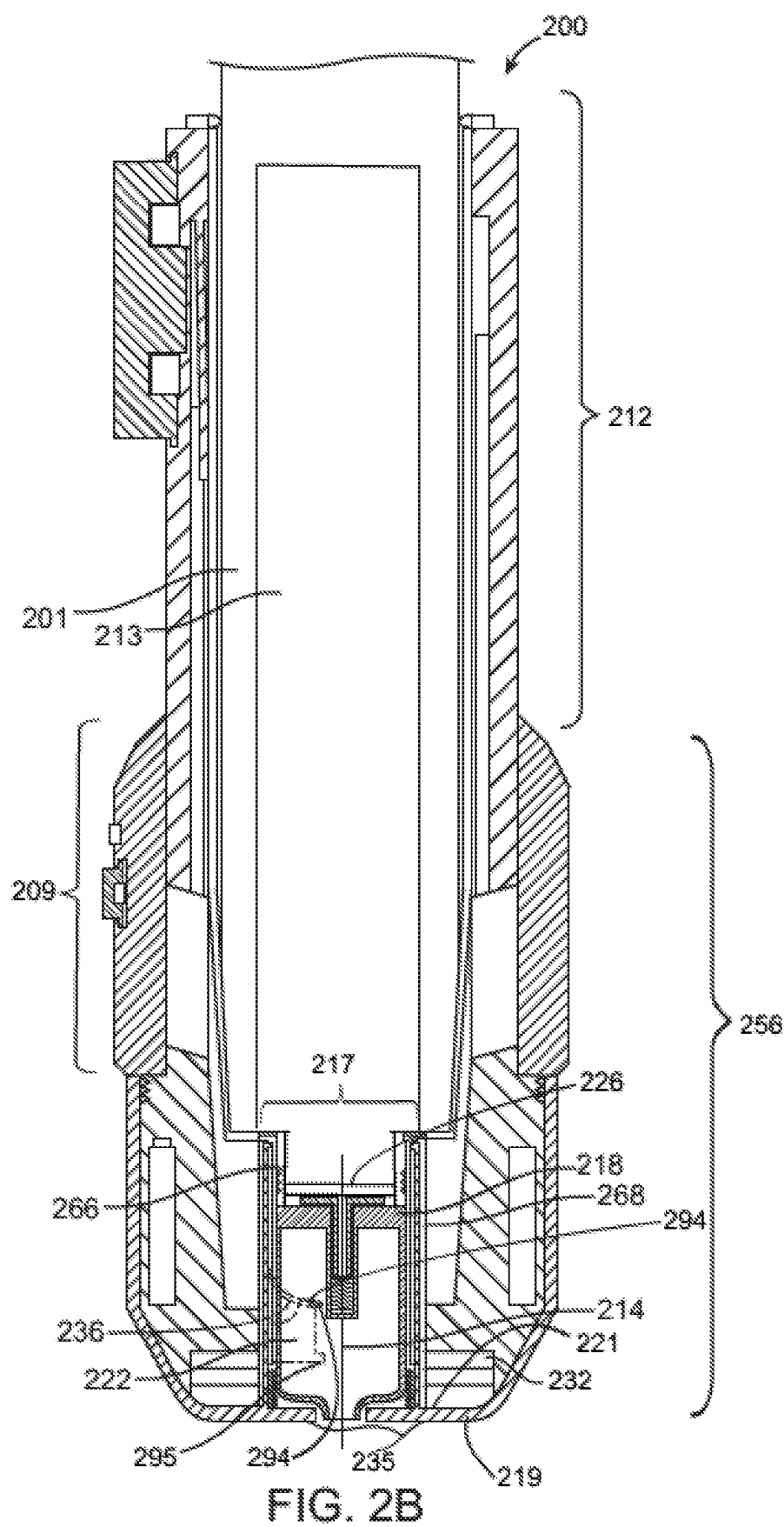

FIGS. 2A and 2B shows an injection apparatus with a cap removed and a cross-section view of a needle assembly 211. FIG. 2A and FIG. 2B show the pain-reducing injection apparatus 200 receiving an injector 201 and a needle assembly 211. FIG. 2A shows the pain-reducing injection apparatus 200 comprising a needle assembly 211 with a needle 214 that is retracted (i.e., not yet deployed). FIG. 2B shows the pain-reducing injection apparatus 200 comprising a needle assembly 211 with a needle 214 that is deployed. In some embodiments, the pain-reducing injection apparatus 200 comprises a pen-type injector sleeve. In some embodiments, the pen-type injector sleeve comprises a lower body 256 and an upper body 212. In some embodiments, the pain-reducing injection apparatus 200 comprises a pain-reducing injection apparatus housing 215. In some embodiments, the injector 201 comprises a reservoir 213 containing an injection fluid (e.g., a medicament). In some embodiments, the lower body 256 contains a battery 260, a vibrator 230, and a thermoelectric cooler 232. In some embodiments, the lower body operatively and reversibly receives a needle assembly 211. In some embodiments, a needle cap (not shown in FIG. 2) reversibly attaches to the needle assembly 211. In some embodiments, the needle cap protects the user from an unwanted or accidental needle puncture. In some embodiments, the needle cap protects the needle from foreign contaminants such as but not limited to bacteria, fungi, and/or viruses.

Referring to FIG. 2A, in some embodiments, the proximal end 205 of the device is defined as the end of the device that is closer to the hand of a user; i.e., the proximal end 205 is towards the upper body 212 of the device. In some embodiments, the distal end 207 of the device is defined as the end of the device that is closer to the injection site of a user or of a patient; i.e., the distal end 207 is towards the lower body 256 of the device. In some embodiments, the upper body 212 of the device and lower body 256 of the device only translocate in the longitudinal axis of the device in a proximal and distal direction, but not in a polar axis of the device; i.e., the upper body 212 of the device and lower body 256 of the device do not rotate with respect to one another.

In some embodiments, the needle assembly 211 comprises an inner sleeve 266 and an outer containing cylinder 268. In some embodiments, the inner sleeve 266 and an outer containing cylinder 268 translocate only in the longitudinal directions as well, relative to each other and relative to the upper body 212 and lower body 256 of the device. In some embodiments, the needle assembly 211 comprises a proximal needle shield 220 and a distal needle shield 264. In some embodiments, the distal needle shield 264 translocates in a longitudinal direction as well as in a polar direction. In some embodiments, the distal needle shield 264 is able to rotate with respect to the inner sleeve 266 and to the outer containing cylinder 268.

In some embodiments, a cylindrical aperture located at the proximal end 205 of the upper body 212 of the device is configured to receive the injector 201. In some embodiments, the cylindrical aperture is slightly larger in diameter than that of the injector 201. In some embodiments, the upper body 212 of the device is configured to receive the injector 201. In some embodiments, the upper body 212 comprises at least one projection or groove (not shown in FIGS. 2A and 2B), as described supra, that reversibly secure the injector 201 into the upper body 212. In some embodiments, the injector 201 fits snuggly within the upper body 212 when loaded onto or into the pen-injector type sleeve. In some embodiments, once secured, the injector aligns with a gasket 226 at the distal end of the upper body 212. In some embodiments, the gasket 226 is a rubber gasket. in some embodiments, the gasket is a re-sealable gasket. In some embodiments, the gasket is penetrated by the needle 214 when the needle assembly 211 is attached to the injector 201.

In some embodiments, the attachments alternatively take different forms. For example, in certain embodiments, the upper body 212 of the device comprises a chuck style clamp or at least one fastener to reversibly secure the injector 201. Furthermore, in yet other embodiments, the upper body 212 of the device comprises a screwing mechanism to screw directly to a distal end of the injector 201.

FIG. 2A shows the upper body 212 of the device having an insertion activation button 208 that is depressed by the user to allow for the insertion of the needle 214 into the skin and/or tissue of a user or patient. In some embodiments, the insertion activation button 208 is depressed to access and/or clean the distal tip of the injector 201 when the needle assembly 211 is not attached to the device (e.g., before and after using the device) without the need to remove the injector 201 from the upper body 212 of the device. In some embodiments, the upper body 212 of the device is attached to a lower body 256 of the device at its distal end by a flexible collar (not shown in FIG. 2). In some embodiments, the upper body 212 and the lower body 256 translate slidably in a cylinder formed by an aperture in the lower body. In some embodiments, the insertion activation button 208 comprises a first insertion activator reset spring 228a and a second insertion activator resent spring 228b. In some embodiments, the first insertion activator reset spring 228a and the second insertion activator resent spring 228b are positioned in between the insertion activation button 208 and the upper body insertion blocking piece 262. In some embodiments, the first insertion activator reset spring 228a and the second insertion activator resent spring 228b are positioned in a first groove or first cavity of the insertion activation button 208 and in a second groove or second cavity insertion activation button 208, respectively, that is configured to receive the insertion activator resent springs. In some embodiments, the first insertion activator reset spring 228a and a second insertion activator resent spring 228b activates the insertion and/or deployment of a needle. In some embodiments, a proximal cylinder (not shown in FIG. 2) of the lower body 256 has walls which extend proximally within walls of the upper body 212. In some embodiments, the walls of the lower body 256 contain two recesses referred to as a first lower body insertion wing recess 278a and a second lower body insertion wing recess 278b. The first lower body insertion wing recess 278a and the second lower body insertion wing recess 278b are configured to accept a first upper body insertion wing 276a and a second upper body insertion wing 276b. In some embodiments, the first upper body insertion wing 276a and a second upper body insertion wing 276b are configured to be slidably moved into the first lower body insertion wing recess 278a and the second lower body insertion wing recess 278b. In some embodiments, the first upper body insertion wing 276a and a second upper body insertion wing 276b are used for stabilization of the device and to limit the maximum length of insertion of the upper body 212 of the device into the lower body 256 of the device when the needle assembly 211 is not present. In some embodiments, the proximal walls of the lower body 256 comprise a lower body insertion blocking piece 263 which abuts an upper body insertion blocking piece 262. In some embodiments, the upper body insertion blocking piece 262 is composed of a semi-flexible material. In some embodiments, the distal end of the upper body insertion blocking piece 262 is bent slightly laterally so as to prevent any distal translocation of the upper body 212. In some embodiments, these components keep the upper body 212 in the farthest proximal location possible relative to the lower body 256 of the device. In some embodiments, the lower body insertion blocking piece 263 and the upper body insertion blocking piece 262 are manipulated by the user by depressing the insertion activation button 208 on the upper body 212. In some embodiments, depressing the insertion activation button 208 pushes the distal end of the upper body insertion blocking piece 262 medially and out of contact with the lower body insertion blocking piece 263, thereby allowing the upper body 212 to translocate in the distal direction relative to the lower body 256.

In some embodiments, the user activates the insertion activation button 208 by depressing the button in order to extend the needle 214 to an exposed position and allow it to penetrate the skin and/or tissue of the patient. In some embodiments, the user additionally applies moderate pressure on the upper body 212 of the device in the distal direction in order to extend the needle 214 to an exposed position and allow it to penetrate the skin and/or tissue of the patient. In some embodiments, the upper body 212 translocates distally and slides until the inner sleeve 266 and the needle 214 reach their maximum insertion depth. In some embodiments, the needle 214 is affixed to the inner sleeve 266. In some embodiments, the maximum insertion depth of the needle 214 (i.e., inner sleeve 266 as well) corresponds to the depth of lower body insertion stopping piece 203 relative to the initial location of the upper body insertion blocking piece 262, thereby also controlling the depth of insertion while the needle assembly 211 is present. In some embodiments, if the needle assembly 211 is removed from the lower body 256 of the device and manual pressure is applied to the upper body 212 in a distal direction relative to the lower body 256 while depressing the insertion activation button 208, the upper body 212 translocates in the distal direction relative to the lower body 256 and the upper body insertion blocking piece 262 stops at the lower body insertion stopping piece 203. In some embodiments, if the insertion activation button 208 is depressed a second time while in this position, the upper body insertion blocking piece 262 is then released in a medial direction from the lower body insertion stopping piece 203 and allow it to slidably advance to its most distal allowable position.

In some embodiments, this distal translocation of the upper body 212 is then halted when a first upper body wing 276a and a second upper body wing 276b slidably stop at a distal end of a first lower body insertion wing recess 278a and a second lower body insertion wing recess 278b, respectively. In some embodiments, in this most collapsed configuration, the distal tip of the repeat injector is easily accessed and cleaned with sanitizing wipes. The ability to clean and sanitize the distal tip of the repeat injector provides various advantages which include, but are not limited to decreasing the likelihood of infection for a patient before use and preventing a transmittable disease from infecting any subsequent patients. In some embodiments, the distal tip of the injector position is unable to be reached while the needle cap is present because the inner sleeve 266 is stopped from distally advancing further. In some embodiments, when the needle assembly 211 is attached to the pain-reducing injection apparatus 200, the inner sleeve 266 does not distally advance sufficiently enough to expose the distal tip of the injector because a ledge (not shown in FIG. 2A and FIG. 2B) on the internal aspect of the outer sleeve 268, blocks it from doing so. In some embodiments, the ledge (not shown in FIG. 2A and FIG. 2B) on the internal aspect of the outer sleeve 268 creates a maximum insertion depth for the needle 214.

FIG. 2A shows the lower body 212 of the device containing a thermoelectric cooling and vibration activator 258 and a light indicator 254. In some embodiments, the light indicator 254 turns on when a user activates the thermoelectric cooling function of the device and/or activates the vibration function of the device. In some embodiments, the light indicator 254 is a light-emitting diode (LED). In some embodiments, the light indicator 254 will flash until the thermoelectric cooling function has reached a desired temperature. In some embodiments, the light indicator 254 comprises a first LED of a first color and a second LED of a second color. In some embodiments, the first LED turns on when the thermoelectric function is activated and the second LED turns on when the vibration function is activated.

In some embodiments, the thermoelectric cooling and vibration activator 258 is a button. In some embodiments, the thermoelectric cooling and vibration activator 258 is a switch. In some embodiments, when the thermoelectric cooling and vibration activator 258 is activated by a user, the thermoelectric cooling and vibration activator 258 activates an electric current through embedded wiring from a battery 260 to the thermoelectric cooler 232, thereby providing electric power to and turning the thermoelectric cooler 232 on. In some embodiments, the thermoelectric cooling and vibration activator 258 is located on the proximal end of the lower body 212 of the pain-reducing injection apparatus 200. In some embodiments, the light indicator 254 is operatively connected to the thermoelectric cooling and vibration activator 258, to the thermoelectric cooler 232 and to the vibrator 230. In some embodiments, the activation of the thermoelectric cooling and vibration activator 258 sends a signal to the light indicator 254 to turn on and display a colored light that notifies the user that the thermoelectric cooler 232 and/or vibrator 230 is activated. In some embodiments, the thermoelectric cooler and vibration activation button spring 271 is operatively connected to the thermoelectric cooler and vibration activation button 258. In some embodiments, the thermoelectric cooler and vibration activation button spring 271 is positioned directly below the thermoelectric cooler and vibration activation button 258. In some embodiments, the thermoelectric cooler and vibration activation button spring 271 is positioned directly adjacent to the thermoelectric cooler and vibration activation button 258. In some embodiments, the thermoelectric cooler and vibration activation button spring 271 is activates the thermoelectric cooler and vibration activation button 258.

Thermoelectric Cooling System

Disclosed herein, in certain embodiments, are pain-reducing injection apparatuses, comprising: a pen-type injector sleeve comprising: a housing configured to operatively receive a drug delivery device, the housing comprising a distal end comprising a distal wall between an inner surface and an active-cooling surface positioned to contact an injection region of an individual when in use; and a thermoelectric cooling system comprising: a thermoelectric cooler comprising a cooling plate, the thermoelectric cooler mounted against the inner surface of the distal end and configured to cool the active-cooling surface by conduction; and a controller operatively coupled to the thermoelectric cooler.

In some embodiments, the drug delivery device is an injector pen. In some embodiments, the drug delivery device is a syringe. In some embodiments, the drug delivery device is a jet injector. In some embodiments, the housing 215 is configured to reversibly receive the drug delivery device. In some embodiments, the housing 215 is configured to permanently receive the drug delivery device.

The thermoelectric cooler functions based on the Peltier effect; namely, it creates a heat flux between the junction of two different types of materials. In some embodiments, the thermoelectric cooler has a first side and a second side which upon application of a direct current (DC) electric current, heat is transferred from the first side to the second side. In some embodiments, the thermoelectric cooler decreases the temperature of a distal side of the thermoelectric cooler and increases the temperature of a proximal side of the thermoelectric cooler.

In some embodiments, the pain-reducing injection apparatus comprises a thermoelectric cooling system. In some embodiments, the thermoelectric cooling system comprises a thermoelectric cooler further comprising a cooling plate (not shown in FIGS. 2A and 2B). In some embodiments, the thermoelectric cooling system comprises a thermoelectric cooler further comprising a heating plate (not shown in FIGS. 2A and 2B). In some embodiments, the thermoelectric cooler is mounted against the inner surface 221 of the distal end of the housing 215, as shown in FIG. 2B. In some embodiments, the inner surface 221 is an inner surface of a distal wall 219, as shown in FIG. 2B. In some embodiments, the thermoelectric cooler 232 sits adjacent and makes thermal contact with the inner surface 221. In some embodiments, thermoelectric cooler 232 is mounted against the inner surface 221 of the distal end of the housing 215. In some embodiments, the thermoelectric cooler transfers heat from an injection region, to an active cooling surface 235, through a distal wall 219, to the inner surface 221 of the distal end of the housing, to the cooling plate of the thermoelectric cooler, and finally to the heating plate and heat sink of the thermoelectric cooler; thereby reducing the surface temperature of the injection region of a patient and/or user. In some embodiments, the heat transferred to the heating plate and/or the heat sink of the thermoelectric cooler is dissipated. In some embodiments, the thermoelectric cooler is configured to cool the active-cooling surface 235 by conduction. In some embodiments, the active-cooling surface 235 is a flat, circular surface surrounding the opening where the needle exits the needle assembly 211. In some embodiments, the active-cooling surface 235 is a distal surface at a distal end of the pain-reducing injection apparatus. In some embodiments, the active-cooling surface 235 is a surface of a housing of the pain-reducing injection apparatus. In some embodiments, the active-cooling surface 235 is composed of a thermally conductive material. In some embodiments, the active-cooling surface 235 is composed of a metal or a metal alloy. In some embodiments, thermoelectric cooling system comprises a controller (not shown in FIGS. 2A and 2B). In some embodiments, the controller is operatively coupled to the thermoelectric cooler. In some embodiments, the cooling plate is mounted against the inner surface of the distal end of the pain-reducing injection apparatus housing. In some embodiments, the cooling plate is configured to cool the active-cooling surface by conduction. In some embodiments, the cooling plate is composed of a thermally insulating material. In some embodiments, the cooling plate is a ceramic plate. In some embodiments, the controller controls a temperature of the cooling plate. In some embodiments, the thermoelectric cooling system comprises a power source operatively coupled to the thermoelectric cooler and to the controller. In some embodiments, the power source is the battery 260. In some embodiments, the battery 260 is a nickel cadmium (NiCd) battery, nickel-metal hydride (NiMH) battery, a nickel zinc (NiZn) battery, a lead acid battery, a lithium ion battery (Li-ion), or a lithium ion polymer (Li-ion polymer) battery.

In some embodiments, the thermoelectric cooling system comprises a temperature sensor (not shown in FIGS. 2A and 2B). In some embodiments, the temperature sensor is operatively connected to the controller. In some embodiments, the temperature sensor is operatively connected the thermoelectric cooler. In some embodiments, the temperature sensor is operatively connected the active-cooling surface. In some embodiments, the temperature sensor is configured to detect a temperature of the cooling plate. In some embodiments, the temperature sensor is configured to detect a temperature of the active-cooling surface 235. In some embodiments, the thermoelectric cooling system comprises a heating plate facing away from the inner surface of the distal end of the pain-reducing injection apparatus housing 215. In some embodiments, the heating plate is in thermal connection with a heat sink. In some embodiments, the heat sink absorbs heat emitted by the heating plate. In some embodiments, the thermoelectric cooling system comprises a fan. In some embodiments, the fan is configured to dissipate heat emitted by the heating plate.

In some embodiments, the cooling plate and the heating plate of the thermoelectric cooler are separated by a material that does not conduct heat. In some embodiments, the controller controls and/or limits the length of time when the thermoelectric cooler is activated. In some embodiments, the controller controls and/or limits the activation of the thermoelectric cooler. In some embodiments, the temperature sensor provides a feedback signal to the controller. In some embodiments, the feedback signal is a temperature of the cooling plate, a temperature of the heating plate, and/or the temperature of the active-cooling surface 235. In some embodiments, the temperature sensor assists the controller in controlling and/or limiting the length of time when the thermoelectric cooler is activated. In some embodiments, the temperature sensor assists the controller in controlling and/or limiting the activation of the thermoelectric cooler. In some embodiments, the thermoelectric cooling system further comprises a limits the length of time when the thermoelectric cooler is activated. In some embodiments, the thermoelectric cooler absorbs heat from a skin surface of a patient. In some embodiments, the thermoelectric cooler absorbs heat from a skin surface of a patient by direct contact between the cooled active-cooling surface 235 and the skin surface. In some embodiments, the absorption of heat from the skin surface of the patient creates an anesthetic effect in underlying tissue.

In some embodiments, the active-cooling surface 235 is cooled to a temperature ranging between about at least −10 to about 10 degrees Celsius or more. In some embodiments, the active-cooling surface 235 is cooled to a temperature ranging between about at least −10 to about 5 degrees Celsius or more. In some embodiments, the active-cooling surface 235 is cooled to a temperature ranging between at least about −10 to about 0 degrees Celsius or more. In some embodiments, the active-cooling surface 235 is cooled to a temperature ranging between at least about −10 to about −5 degrees Celsius or more. In some embodiments, the active-cooling surface 235 is cooled to a temperature ranging between at least about −15 to about 15 degrees Celsius or more. In some embodiments, the active-cooling surface 235 is cooled to a temperature ranging between at least about −15 to about 10 degrees Celsius or more. In some embodiments, the active-cooling surface 235 is cooled to a temperature ranging between at least about −15 to about 5 degrees Celsius or more. In some embodiments, the active-cooling surface 235 is cooled to a temperature ranging between at least about −15 to about 0 degrees Celsius or more. In some embodiments, the active-cooling surface 235 is cooled to a temperature ranging between at least about −15 to about −5 degrees Celsius or more. In some embodiments, the active-cooling surface 235 is cooled to a temperature ranging between at least about −15 to about −10 degrees Celsius or more.

In some embodiments, the active-cooling surface 235 is cooled to a temperature of about −15 degrees Celsius. In some embodiments, the active-cooling surface 235 is cooled to a temperature of about −14 degrees Celsius. In some embodiments, the active-cooling surface 235 is cooled to a temperature of about −13 degrees Celsius. In some embodiments, the active-cooling surface 235 is cooled to a temperature of about −12 degrees Celsius. In some embodiments, the active-cooling surface 235 is cooled to a temperature of about −11 degrees Celsius. In some embodiments, the active-cooling surface 235 is cooled to a temperature of about −10 degrees Celsius. In some embodiments, the active-cooling surface 235 is cooled to a temperature of about −9 degrees Celsius. In some embodiments, the active-cooling surface 235 is cooled to a temperature of about −8 degrees Celsius. In some embodiments, the active-cooling surface 235 is cooled to a temperature of about −7 degrees Celsius. In some embodiments, the active-cooling surface 235 is cooled to a temperature of about −6 degrees Celsius. In some embodiments, the active-cooling surface 235 is cooled to a temperature of about −5 degrees Celsius. In some embodiments, the active-cooling surface 235 is cooled to a temperature of about −4 degrees Celsius. In some embodiments, the active-cooling surface 235 is cooled to a temperature of about −3 degrees Celsius. In some embodiments, the active-cooling surface 235 is cooled to a temperature of about −2 degrees Celsius. In some embodiments, the active-cooling surface 235 is cooled to a temperature of about −1 degree Celsius. In some embodiments, the active-cooling surface 235 is cooled to a temperature of about 0 degrees Celsius. In some embodiments, the active-cooling surface 235 is cooled to a temperature of about 1 degree Celsius. In some embodiments, the active-cooling surface 235 is cooled to a temperature of about 2 degrees Celsius. In some embodiments, the active-cooling surface 235 is cooled to a temperature of about 3 degrees Celsius. In some embodiments, the active-cooling surface 235 is cooled to a temperature of about 4 degrees Celsius. In some embodiments, the active-cooling surface 235 is cooled to a temperature of about 5 degrees Celsius. In some embodiments, the active-cooling surface 235 is cooled to a temperature of about 6 degrees Celsius. In some embodiments, the active-cooling surface 235 is cooled to a temperature of about 7 degrees Celsius. In some embodiments, the active-cooling surface 235 is cooled to a temperature of about 8 degrees Celsius. In some embodiments, the active-cooling surface 235 is cooled to a temperature of about 9 degrees Celsius. In some embodiments, the active-cooling surface 235 is cooled to a temperature of about 10 degrees Celsius. In some embodiments, the active-cooling surface 235 is cooled to a temperature of about 11 degrees Celsius. In some embodiments, the active-cooling surface 235 is cooled to a temperature of about 12 degrees Celsius. In some embodiments, the active-cooling surface 235 is cooled to a temperature of about 13 degrees Celsius. In some embodiments, the active-cooling surface 235 is cooled to a temperature of about 14 degrees Celsius. In some embodiments, the active-cooling surface 235 is cooled to a temperature of about 15 degrees Celsius.

In some embodiments, the injection region of a patient is cooled by direct contact with the active-cooling surface 235 of the pain-reducing injection apparatus. In some embodiments, the injection region is cooled to a temperature ranging between about at least −10 to about 10 degrees Celsius or more. In some embodiments, the injection region is cooled to a temperature ranging between about at least −10 to about 5 degrees Celsius or more. In some embodiments, the injection region is cooled to a temperature ranging between at least about −10 to about 0 degrees Celsius or more. In some embodiments, the injection region is cooled to a temperature ranging between at least about −10 to about −5 degrees Celsius or more. In some embodiments, the injection region is cooled to a temperature ranging between at least about −15 to about 15 degrees Celsius or more. In some embodiments, the injection region is cooled to a temperature ranging between at least about −15 to about 10 degrees Celsius or more. In some embodiments, the injection region is cooled to a temperature ranging between at least about −15 to about 5 degrees Celsius or more. In some embodiments, the injection region is cooled to a temperature ranging between at least about −15 to about 0 degrees Celsius or more. In some embodiments, the injection region is cooled to a temperature ranging between at least about −15 to about −5 degrees Celsius or more. In some embodiments, the injection region is cooled to a temperature ranging between at least about −15 to about −10 degrees Celsius or more.

In some embodiments, the injection region is cooled to a temperature of about −15 degrees Celsius. In some embodiments, the injection region is cooled to a temperature of about −14 degrees Celsius. In some embodiments, the injection region is cooled to a temperature of about −13 degrees Celsius. In some embodiments, the injection region is cooled to a temperature of about −12 degrees Celsius. In some embodiments, the injection region is cooled to a temperature of about −11 degrees Celsius. In some embodiments, the injection region is cooled to a temperature of about −10 degrees Celsius. In some embodiments, the injection region is cooled to a temperature of about −9 degrees Celsius. In some embodiments, the injection region is cooled to a temperature of about −8 degrees Celsius. In some embodiments, the injection region is cooled to a temperature of about −7 degrees Celsius. In some embodiments, the injection region is cooled to a temperature of about −6 degrees Celsius. In some embodiments, the injection region is cooled to a temperature of about −5 degrees Celsius. In some embodiments, the injection region is cooled to a temperature of about −4 degrees Celsius. In some embodiments, the injection region is cooled to a temperature of about −3 degrees Celsius. In some embodiments, the injection region is cooled to a temperature of about −2 degrees Celsius. In some embodiments, the injection region is cooled to a temperature of about −1 degree Celsius. In some embodiments, the injection region is cooled to a temperature of about 0 degrees Celsius. In some embodiments, the injection region is cooled to a temperature of about 1 degree Celsius. In some embodiments, the injection region is cooled to a temperature of about 2 degrees Celsius. In some embodiments, the injection region is cooled to a temperature of about 3 degrees Celsius. In some embodiments, the injection region is cooled to a temperature of about 4 degrees Celsius. In some embodiments, the injection region is cooled to a temperature of about 5 degrees Celsius. In some embodiments, the injection region is cooled to a temperature of about 6 degrees Celsius. In some embodiments, the injection region is cooled to a temperature of about 7 degrees Celsius. In some embodiments, the injection region is cooled to a temperature of about 8 degrees Celsius. In some embodiments, the injection region is cooled to a temperature of about 9 degrees Celsius. In some embodiments, the injection region is cooled to a temperature of about 10 degrees Celsius. In some embodiments, the injection region is cooled to a temperature of about 11 degrees Celsius. In some embodiments, the injection region is cooled to a temperature of about 12 degrees Celsius. In some embodiments, the injection region is cooled to a temperature of about 13 degrees Celsius. In some embodiments, the injection region is cooled to a temperature of about 14 degrees Celsius. In some embodiments, the injection region is cooled to a temperature of about 15 degrees Celsius.

In some embodiments, the injection region of the patient is cooled to a temperature of about 10 degrees Celsius by direct contact between the injection region and the active-cooling surface 235. In some embodiments, when the injection region reaches a desired temperature (e.g., 10 degrees Celsius), the temperature sensor sends a feedback signal to inactivate the thermoelectric cooler. In some embodiments, the feedback signal triggers a change in the color of the indicator light 254. In some embodiments, the change in color of the indicator light 254 notifies the user that the injection region is at the correct temperature and appropriately anesthetized for needle insertion.

In some embodiments, the injection region is contacted with the active-cooling surface 235 for at least about 1 minute to about 5 minutes or more prior to insertion of the needle. In some embodiments, the injection region is contacted with the active-cooling surface 235 for at least about 15 seconds to about 10 minutes or more prior to insertion of the needle. In some embodiments, the injection region is contacted with the active-cooling surface 235 for at least about 30 seconds to about 10 minutes or more prior to insertion of the needle. In some embodiments, the injection region is contacted with the active-cooling surface 235 for at least about 45 seconds to about 10 minutes or more prior to insertion of the needle. In some embodiments, the injection region is contacted with the active-cooling surface 235 for at least about 1 minute to about 10 minutes or more prior to insertion of the needle. In some embodiments, the injection region is contacted with the active-cooling surface 235 for at least about 2 minutes to about 5 minutes or more prior to insertion of the needle. In some embodiments, the injection region is contacted with the active-cooling surface 235 for at least about 1 minute to about 5 minutes or more prior to insertion of the needle. In some embodiments, the injection region is contacted with the active-cooling surface 235 for at least about 3 minutes to about 5 minutes or more prior to insertion of the needle.

In some embodiments, the injection region is contacted with the active-cooling surface 235 for about 5 seconds prior to insertion of the needle. In some embodiments, the injection region is contacted with the active-cooling surface 235 for about 10 seconds prior to insertion of the needle. In some embodiments, the injection region is contacted with the active-cooling surface 235 for about 15 seconds prior to insertion of the needle. In some embodiments, the injection region is contacted with the active-cooling surface 235 for about 30 seconds prior to insertion of the needle. In some embodiments, the injection region is contacted with the active-cooling surface 235 for about 45 seconds prior to insertion of the needle. In some embodiments, the injection region is contacted with the active-cooling surface 235 for about 1 minute prior to insertion of the needle. In some embodiments, the injection region is contacted with the active-cooling surface 235 for about 2 minutes prior to insertion of the needle. In some embodiments, the injection region is contacted with the active-cooling surface 235 for about 3 minutes prior to insertion of the needle. In some embodiments, the injection region is contacted with the active-cooling surface 235 for about 4 minutes prior to insertion of the needle. In some embodiments, the injection region is contacted with the active-cooling surface 235 for about 5 minutes prior to insertion of the needle. In some embodiments, the injection region is contacted with the active-cooling surface 235 for about 6 minutes prior to insertion of the needle. In some embodiments, the injection region is contacted with the active-cooling surface 235 for about 7 minutes prior to insertion of the needle. In some embodiments, the injection region is contacted with the active-cooling surface 235 for about 8 minutes prior to insertion of the needle. In some embodiments, the injection region is contacted with the active-cooling surface 235 for about 9 minutes prior to insertion of the needle. In some embodiments, the injection region is contacted with the active-cooling surface 235 for about 10 minutes prior to insertion of the needle. In some embodiments, the injection region is contacted with the active-cooling surface 235 for about 15 minutes prior to insertion of the needle.

Vibrator

Disclosed herein, in certain embodiments, are pain-reducing injection apparatuses, comprising: a pen-type injector sleeve comprising: a housing configured to operatively receive a drug delivery device, the housing comprising a distal surface located at a distal region of the housing, the distal surface positioned to contact an injection region of an individual when in use; and a vibrator mounted in the housing, the vibrator configured to cause a distal region of the housing to vibrate.

In some embodiments, the vibrator 230 is activated by a user depressing the cold and vibration activation button 208. Alternatively, in other embodiments, the vibrator 230 is activated remotely or by activation of an additionally button and/or switch. In some embodiments, the vibrator 230 creates vibrations that are transmitted through the distal end of the needle assembly surface. In some embodiments, the vibrator 230 generates vibrations that further increase the anesthetic effect perceived by the patient. In some embodiments, activation of the vibrator 230 is controlled by the controller. In some embodiments, activation of the vibrator 230 is stopped based on the activation time of the thermoelectric cooler.

In some embodiments, the distal surface of the pain-reducing injection apparatus housing 215 is vibrating when the needle is inserted into the injection region of the individual. In some embodiments, the needle is vibrating when the needle is inserted into the injection region of the individual. In some embodiments, the vibration has a vibration frequency ranging from about 100 Hertz (Hz) to about 300 Hz. In some embodiments, the vibration has an amplitude ranging from about 0.3 G (wherein G is gravitational acceleration, i.e., 9.8 meters per second squared) to about 125 G. In some embodiments, the vibrator is configured to cause the active-cooling surface, the drug delivery device, and/or a needle to vibrate. In some embodiments, the vibrator comprises a motor. In some embodiments, the motor is an eccentric rotating mass vibration motor or a linear resonant actuator.

Further disclosed herein, in certain embodiments, are pain-reducing injection apparatuses, comprising: a pen-type injector sleeve comprising: a housing configured to operatively receive a drug delivery device, the housing comprising a distal end comprising a distal wall between an inner surface and an active-cooling surface positioned to contact an injection region of an individual when in use; a thermoelectric cooler comprising a cooling plate mounted against the inner surface of the distal end and configured to cool the active-cooling surface by conduction; and a vibrator mounted in the housing, the vibrator configured to cause the distal end of the housing to vibrate.

In some embodiments, the control of the activation and inactivation of the vibration and thermoelectric cooler is automatically triggered by attaching the needle assembly 211 to the pain-reducing injection apparatus housing 215. In some embodiments the needle assembly comprises a needle and a needle hub. In some embodiments, the needle assembly is a needle assembly other than the one described herein in FIGS. 2A-B and 3A-D. In some embodiments, the control of the activation and inactivation of the vibration and thermoelectric cooler is automatically triggered by a mechanism that detects pressure on the distal end of the lower body 256 and a needle assembly surface. The device could also contain other types of pain reducing units and modalities that could be transmitted through the needle cap to anesthetize the patient's skin such as direct electrical pulses among others, while the cap still creates a barrier protecting the cleanliness, sterility, and safety of the device and injector or syringe.

Needle Assembly

Additionally disclosed herein, in certain embodiments, are pain-reducing injection apparatuses, comprising: a pen-type injector sleeve comprising: a housing configured to operatively receive a drug delivery device, the housing comprising a distal surface located at a distal region of the housing, the distal surface configured to contact an injection region of an individual when in use; and a needle assembly comprising: a needle, an outer sleeve having a first inner surface comprising a ramped track, and a first outer surface, an inner sleeve positioned within the outer sleeve, the inner sleeve comprising: a second inner surface, a second outer surface facing the first inner surface, an aperture comprising a perimeter and a perimeter wall extending between the second inner surface and the second outer surface along the perimeter, and a distal needle insertion shield coaxially aligned with the inner sleeve and with the outer sleeve, the distal needle insertion shield comprising a distal shield insertion arm configured to travel along the perimeter of the aperture in contact with the perimeter wall of the aperture as the distal needle insertion shield rotates about its axis, and wherein the distal shield insertion arm extends through the aperture and is configured to travel within and along the ramped track as the distal needle insertion shield is axially rotated about the axis.

Also disclosed herein, in certain embodiments, are needle assemblies, comprising: a needle; an outer sleeve having a first inner surface comprising a ramped track, and a first outer surface; an inner sleeve positioned within the outer sleeve, the inner sleeve comprising: a second inner surface, a second outer surface facing the first inner surface, and an aperture comprising a perimeter and a perimeter wall extending between the second inner surface and the second outer surface along the perimeter; and a distal needle insertion shield coaxially aligned with the inner sleeve and with the outer sleeve, the distal needle insertion shield comprising a distal shield insertion arm configured to travel along the perimeter of the aperture in contact with the perimeter wall of the aperture as the distal needle insertion shield rotates about its axis, and wherein the distal shield insertion arm extends through the aperture and is configured to travel within and along the ramped track as the distal needle insertion shield is axially rotated about the axis.

In some embodiments, the needle assembly reversibly attaches to a pen injector. In some embodiments, the needle assembly permanently attaches to a pen injector. In some embodiments, the needle assembly is screwed into a pen injector. In some embodiments, the needle assembly is snapped onto a pen injector. In some embodiments, the needle assembly reversibly attaches to a pain-reducing injection apparatus. In some embodiments, the needle assembly permanently attaches to a pain-reducing injection apparatus. In some embodiments, the needle assembly is screwed into a pain-reducing injection apparatus. In some embodiments, the needle assembly is snapped onto a pain-reducing injection apparatus. In some embodiments, the needle assembly reversibly attaches to a pen-style injector sleeve. In some embodiments, the needle assembly permanently attaches to a pen-style injector sleeve. In some embodiments, the needle assembly is screwed into a pen-style injector sleeve. In some embodiments, the needle assembly is snapped onto a pen-style injector sleeve.

In some embodiments, the needle assembly comprises a needle cap configured to receive the needle assembly. In some embodiments, the needle cap is reusable. In some embodiments, the needle cap protects a needle from external contaminants. In some embodiments, the needle cap protects a user and/or patient from accidental punctures.

In some embodiments, the needle assembly comprises a fingerprint authentication locking mechanism comprising a fingerprint sensor and a needle cap lock. In some embodiments, the needle cap lock is unlocked upon recognition of a fingerprint of a user by the fingerprint sensor. In some embodiments, the fingerprint sensor is located on the needle cap.

Figure 3A:
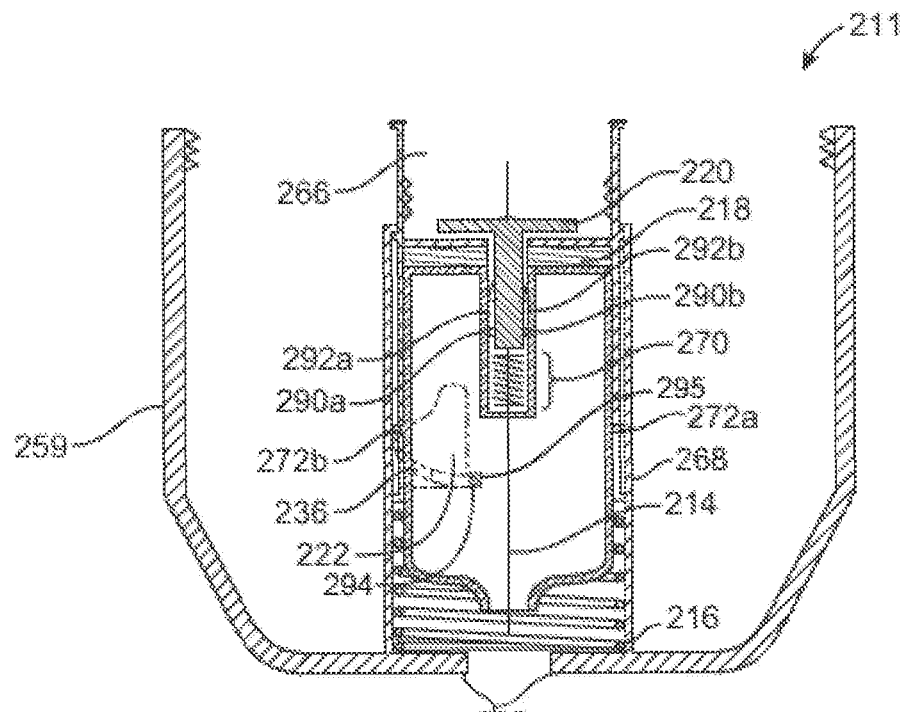
FIGS. 3A, 3B, 3C, and 3D depict an embodiment of internal component view of a replaceable needle assembly for a pain-reducing injection apparatus.

FIGS. 3A, 3B, 3C, and 3D show the needle assembly safety mechanism and its components at various stages of a needle deployment and retraction process. In some embodiments, the needle assembly safety mechanism is designed to retract and lock a needle after deployment and use (e.g., after insertion into an injection region) in order to prevent unwanted disease transmission, punctures, and/or incorrect delivery of a medicament. FIG. 3A shows the needle assembly at its initial (i.e., resting) position and the needle being shielded within the walls of an inner sleeve 266 and an outer sleeve 268. In some embodiments, at this stage, a distal needle shield spring 218 is compressed, a proximal needle shield spring 270 is compressed, and an inner sleeve spring 216 is fully extended. In some embodiments, the components of the needle assembly are encased in or protected by a needle housing 259, as shown in FIGS. 3A, 3B, 3C, and 3D.

In some embodiments, the outer shield 268 comprises a ramped track 236. In some embodiments, the ramped track 236 has a start and a finish and a bump 237 positioned medially therebetween. FIG. 3A shows a second distal needle shield insertion arm 272*b* at the start of the ramped track 236. In some embodiments, the ramped track 236 is angled. In some embodiments, the ramped track is angled at an angle of about 45 degrees with respect to the distal surface of the needle assembly housing. In some embodiments, the distal shield insertion arm travels from the first end of the aperture to the second end of the aperture as the distal needle insertion shield is axially rotated about the axis. In some embodiments, the distal shield insertion arm is resting on the perimeter of the aperture at the first end of the aperture and within the ramped track at start of the ramped track prior to deployment of the needle.

In some embodiments, the outer sleeve 268 comprises an aperture 222. In some embodiments, the aperture 222 has a first end of the aperture and a second end of the aperture. In some embodiments, the first end of the aperture aligns with the start of the ramped track and the second end of the aperture aligns with the finish of the ramped track prior to deployment of the needle. FIG. 3A shows a second distal needle shield insertion arm 272*b* inserted at the first end of the aperture.

Figure 3B:
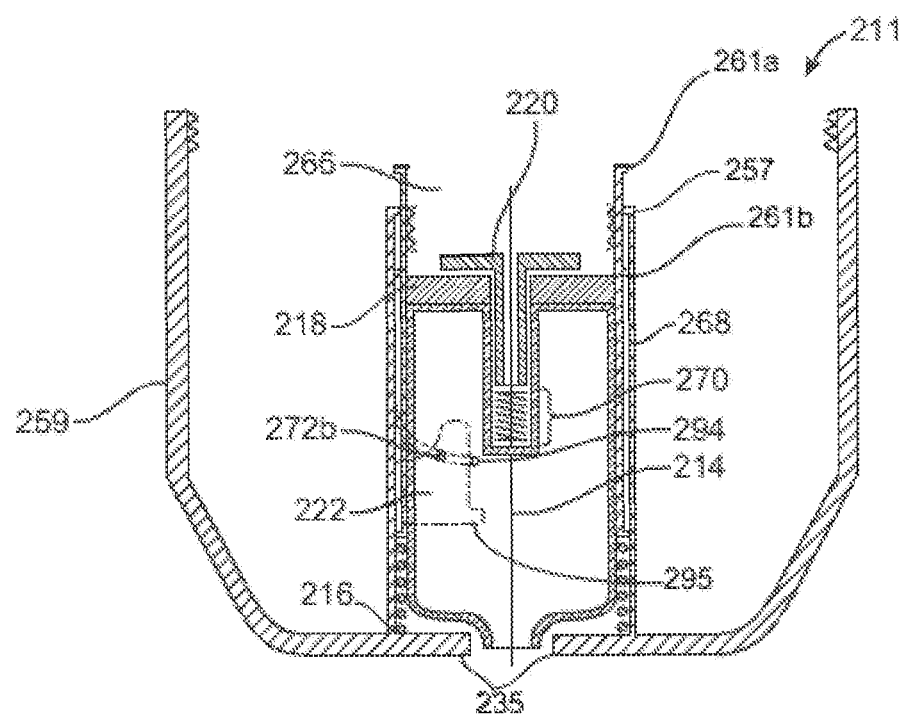

FIG. 3B shows the needle assembly after the needle has started to be deployed (i.e., the needle has been advanced distally away from the proximal region of the needle assembly). FIG. 3B shows the needle starting to exit a needle opening located in the center of a distal wall of the needle assembly. In some embodiments, deployment of the needle from the needle assembly causes the distal shield insertion arm to overcome the bump 237 and subsequently rest within the track 236. In some embodiments, the distal shield insertion arm travels from the start of the ramped track 236 to the finish of the ramped track as the distal needle insertion shield 264 is axially rotated about the axis. In some embodiments, at this stage, the distal needle shield spring 218 is extended, the proximal needle shield spring 270 is compressed, and the inner sleeve spring 216 is compressed. In some embodiments, the distal shield insertion arm travels from the first end of the aperture to the second end of the aperture as the distal needle insertion shield 264 is axially rotated about the axis. In some embodiments, the distal shield insertion arm is resting on the perimeter of the aperture 297 at the first end of the aperture and within the ramped track 236 at start of the ramped track prior to deployment of the needle.

Figure 3C:
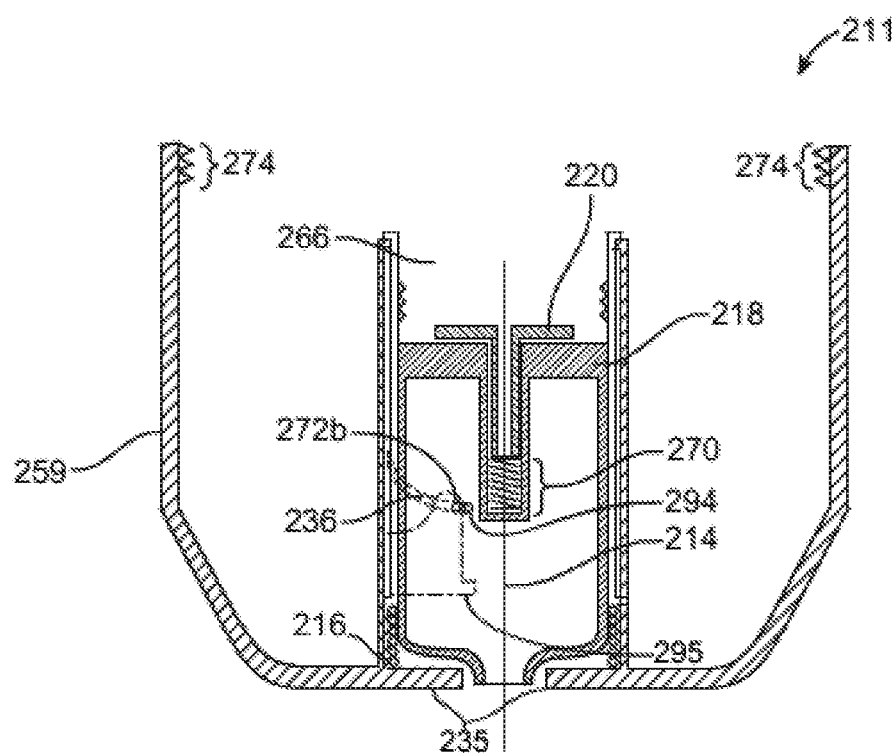

FIG. 3C shows the needle assembly 211 after deployment of the needle 214 has been completed. In FIG. 3C, the needle is shown to be exposed and outside a needle opening. In some embodiments, at this stage, the distal needle shield spring 218 is extended, the proximal needle shield spring 270 is compressed, and the inner sleeve spring 216 is compressed. In some embodiments, the bump 237 prevents the distal shield insertion arm to travel from the finish to the start of the ramped track once the distal shield insertion arm overcomes the bump 237. In some embodiments, the perimeter of the aperture 297 has an aperture locking notch 295 positioned at the second end of the aperture. In some embodiments, the perimeter of the aperture has a sloped region originating from the first end of the aperture 222 and ending at a vertical region of the aperture. In some embodiments, the vertical region of the aperture originates from a peak of the sloped region and ends at the aperture locking notch 295. In some embodiments, the deployment of the needle causes the distal shield insertion arm to rest at the peak of the sloped region, on the perimeter of the aperture.

Figure 3D:
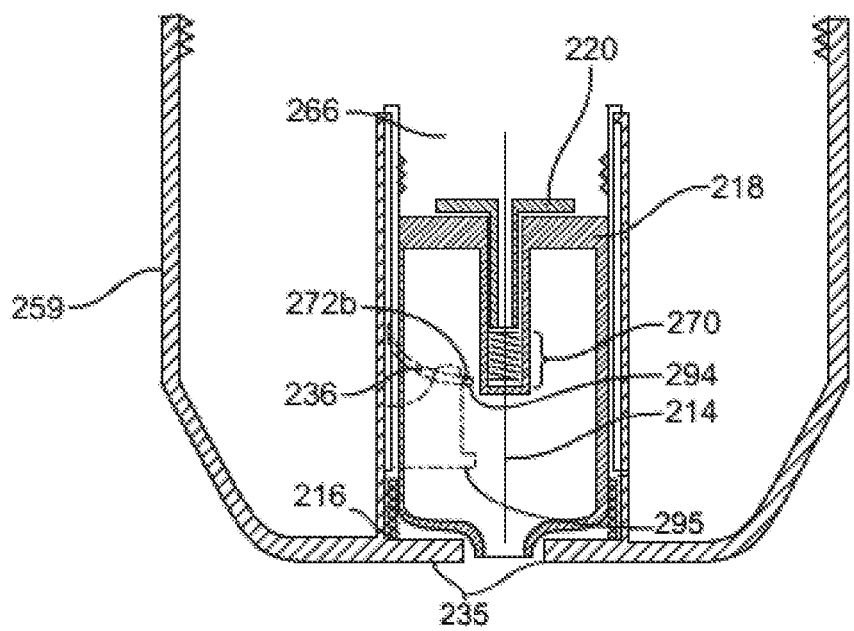

FIG. 3D shows the needle assembly at its final stage, after deployment and use of the needle. FIG. 3D shows the needle retracted and in a locked position; thereby unable to be used and/or deployed again. In some embodiments, the ramped track has a track locking notch 294 positioned at the finish of the ramped track. In some embodiments, the track locking notch 294 is configured to lock the distal shield insertion arm in place after the needle 214 is deployed and retracted. In some embodiments, the aperture locking notch is configured to lock the distal shield insertion arm in place after the needle is deployed and retracted.

Figure 4:
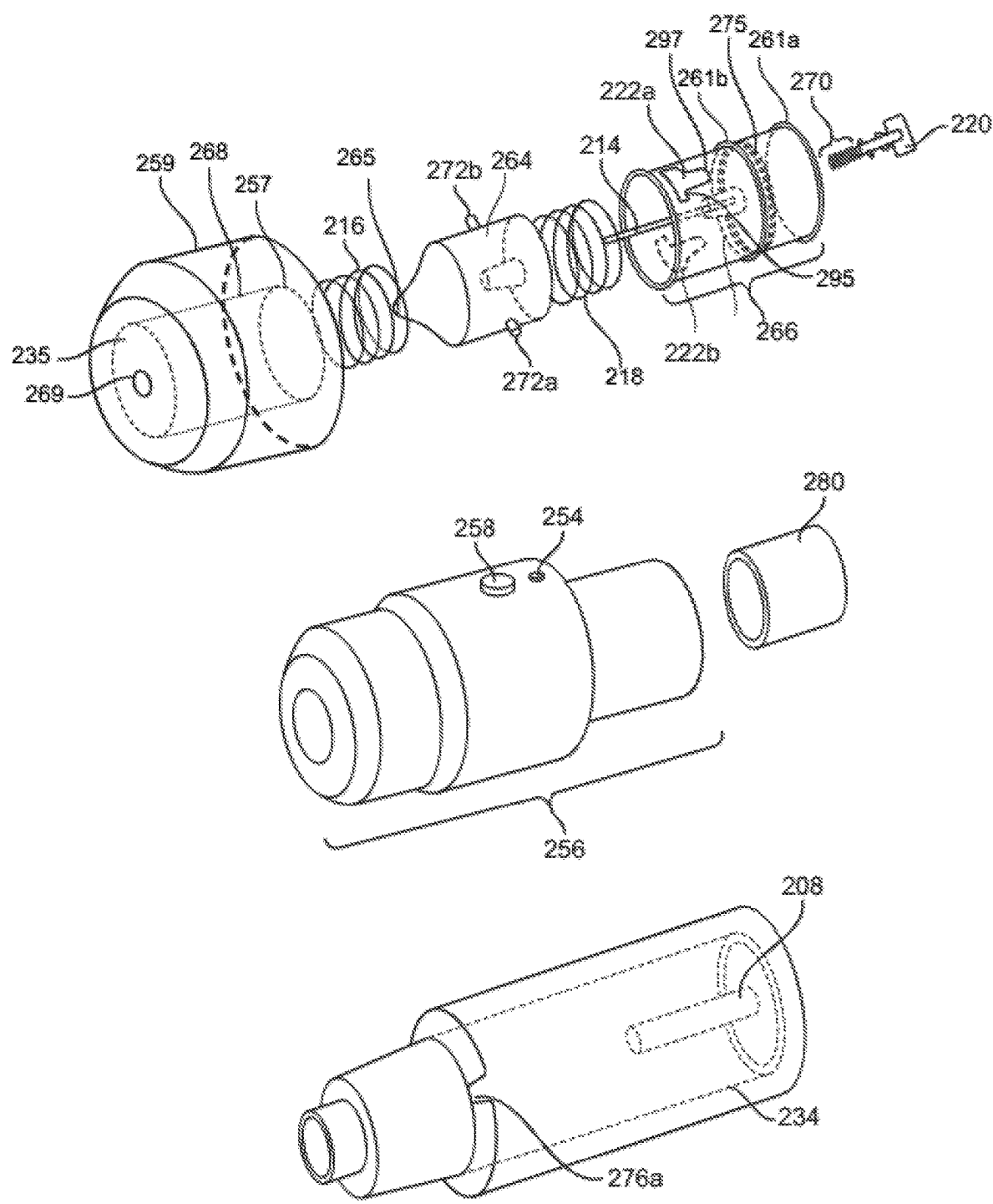
FIG. 4 depicts an embodiment of an exploded component view of a pain-reducing injection apparatus.

FIG. 4 shows an exploded view of the pain-reducing injection apparatus 200. In some embodiments, the distal needle insertion shield 264 is positioned within the inner sleeve 266. In some embodiments, the inner sleeve 266 containing the distal needle insertion shield 264 is positioned within the outer sleeve 268. As shown in FIG. 4, the inner sleeve 266 comprises a first aperture 222a and a second aperture 222b. In some embodiments, the inner sleeve 266 is coaxially aligned with the outer sleeve 268. In some embodiments, the first aperture 222a and the second aperture 222b of the inner sleeve 266 are coaxially aligned with the first ramped track and the second ramped track of outer sleeve 268 (not shown in FIG. 4). In some embodiments, the proximal region of the pain-reducing injection apparatus 200 comprises an insertion activation button 208, a barrel 234, and upper body insertion wings, as shown in FIG. 4.

In some embodiments, the outer sleeve 268 comprises at least one slit (not shown in FIG. 4) configured to receive a distal needle shield insertion arm. In some embodiments, a distal needle insertion arm is inserted into at least one slit of the outer sleeve 268 when inserting the inner sleeve 266 into the outer sleeve 268. In some embodiments, the inner sleeve 266 comprises at least one slit (not shown in FIG. 4) configured to receive a distal needle shield insertion arm. In some embodiments, a distal needle insertion arm is inserted into at least one slit of the inner sleeve 266 when inserting the distal needle shield 264 into the inner sleeve 266. In some embodiments, the outer sleeve 268 comprises at least one outer sleeve ramp (not shown in FIG. 4) connecting to the ramped track, the outer sleeve ramp configured to receive a distal needle shield insertion arm and guide it towards the ramped track 236 when inserting the inner sleeve 266 into the outer sleeve 268. In some embodiments, the inner sleeve 266 comprises at least one inner sleeve ramp (not shown in FIG. 4) connecting to the aperture 222, the inner sleeve ramp configured to receive a distal needle shield insertion arm and guide it towards the aperture 222 when inserting the distal needle shield 264 into the inner sleeve 266.

In some embodiments, the distal needle shield 264 comprises a distal needle shield opening 265, as shown in FIG. 4. In some embodiments, the distal needle shield opening 265 is an opening located at a distal end of the distal needle shield 264, configured to allow the needle 214 to exit therethrough. In some embodiments, the outer sleeve 268 and the needle assembly housing 259 comprises a needle opening 269, as shown in FIG. 4. In some embodiments, the needle opening 269 is an opening located at the distal end of the needle assembly, configured to allow the needle 214 to exit therethrough.

In some embodiments, the outer sleeve 268 comprises an outer sleeve ridge 257, as shown in FIG. 3B and FIG. 4. In some embodiments, the outer sleeve 268 comprises an outer sleeve ridge 257 is configured to align the outer sleeve 268 with the inner sleeve 266. In some embodiments, the outer sleeve ridge 257 is configured to align the outer sleeve 268 with the inner sleeve 266. In some embodiments, the inner sleeve 266 comprises a first inner sleeve ridge 261a and a second inner sleeve ridge 261b, as shown in FIG. 3B and FIG. 4. In some embodiments, the first inner sleeve ridge 261a and the second inner sleeve ridge 261b are configured to align the inner sleeve 266 with the outer sleeve 268.

In some embodiments, the outer sleeve is cylindrical. In some embodiments, the inner sleeve is cylindrical. In some embodiments, the outer sleeve is coaxially aligned with the inner sleeve. In some embodiments, the aperture locking notch is aligned with the track locking notch. In some embodiments, the needle is contained within the inner sleeve prior to deployment. In some embodiments, the ramped track is unidirectional. In some embodiments, the distal shield insertion arm is moved distally as the as the distal needle insertion shield is axially rotated about the axis.

In some embodiments, the distal end 207 of the lower body 212 of the pain-reducing injection apparatus 200 contains a cylindrical aperture (not shown in FIG. 2A, 2B, 3A, 3B, 3C, or 3D) that is slightly wider than the diameter of the outer sleeve 268 of the needle assembly 211. In some embodiments, the cylindrical aperture extends proximally through and beyond the thermoelectric cooler. In some embodiments, a proximal wall of the cylindrical aperture is a distal wall of the flexible collar 280. In some embodiments, the flexible collar 280 (shown in FIG. 4) connects the lower body 256 of the pain-reducing injection apparatus 200 to the upper body 212 of the device pain-reducing injection apparatus 200. In some embodiments, the proximal wall of the cylindrical aperture is a distal end of the upper body 212.

In some embodiments, the lateral walls of the needle assembly 211 attach to the lateral walls of the distal end 207 of the adaptor 209 (shown in FIG. 2B). In some embodiments, the inner sleeve 266 of the needle assembly 211 attach to the distal end of the injector 201. In some embodiments, the diameter of the outer sleeve 268 of the needle assembly 211 is larger than that of the inner sleeve 266. In some embodiments, the inner sleeve has a cylindrical aperture that is wider than a threaded cylinder of the distal end of the injector 201 or a syringe. In some embodiments, the user slides the center column 217 (i.e., the outer sleeve 268 and the inner sleeve 266 encased by the needle assembly housing 259) of the needle assembly 211 into the cylindrical aperture of the adaptor 209 in order to attach the needle assembly 211 to a distal end of the pain-reducing injection apparatus 200. In some embodiments, the user slides the center column 217 of the needle assembly 211 into a cylindrical aperture of the adaptor 209 in order to attach the needle assembly 211 to the distal end of the standard repeating injector 100. In some embodiments, the distal region of the walls of the center column of the needle assembly 211 comprises the exterior walls of the outer sleeve 268. In some embodiments, the proximal region of the walls of the center column of the needle assembly 211 comprises the exterior walls of the inner sleeve 266. In some embodiments, the needle assembly 211 is reversibly attached to the pain-reducing injection apparatus 200 by the user. In some embodiments, the needle assembly 211 is reversibly screwed into or snapped onto the pain-reducing injection apparatus 200. In some embodiments, the inner walls of the proximal region of the inner sleeve 266 attach to the distal end of the injector 200 while the external walls of the needle assembly 211 are attached to the lateral ends of the pain-reducing injection apparatus housing 215. In some embodiments, the needle assembly serves as a barrier to prevent the skin, blood, and/or other various body substances and fluids from contaminating the pain-reducing injection apparatus 200. In some embodiments, the exterior walls of the needle assembly 211 have increased length in a proximal direction relative to the center column 217 of the needle assembly 211. In some embodiments, exterior walls of the needle assembly 211 with an increased length relative to the center column 217 covers provide for a barrier of increased utility for using the pain-reducing injection apparatus 200 to inject into bodily orifices and/or more contaminated areas of a tissue. For example, in some embodiments, the longer needle assembly exterior walls are necessary for procedures such as oral injections.

In some embodiments, the needle assembly 211 has a large cylindrical recess on its proximal side surrounding the inner sleeve 266. In some embodiments, the recess is the same shape of the distal end of the adaptor 209 and fits snuggly to that surface when screwed into place. In some embodiments, the distal end of the recess is composed of a material that is able to conduct the heat from the injection region to the thermoelectric cooler when activated. In some embodiments, the distal end of the recess is composed of a material that is able to conduct vibration to the injection region. In some embodiments, the distal end of the recess is composed of a plastic, a metal, and/or a metal alloy. In some embodiments, the distal end of the needle assembly 211 is able to conduct other anesthetic functions that are present in the lower body 256; for example, electrical pulses, among others. In some embodiments, the needle assembly 211 comprises an active-cooling surface 235. In some embodiments, the active-cooling surface 235 is able to conduct heat away from the injection region. In some embodiments, the active-cooling surface 235 is able to deliver a vibration to an injection region. In some embodiments, conducting heat away from the injection region and/or delivering a vibration to the injection region allows for an anesthetic effect to occur near the needle penetration point, within the injection region.

In some embodiments, the injection region is at least about 0.1 centimeters (cm) to about 5 cm or more away from the needle penetration point. In some embodiments, the injection region is at least about 0.5 centimeters (cm) to about 5 cm or more away from the needle penetration point. In some embodiments, the injection region is at least about 1 centimeters (cm) to about 5 cm or more away from the needle penetration point. In some embodiments, the injection region is at least about 2 centimeters (cm) to about 5 cm or more away from the needle penetration point. In some embodiments, the injection region is at least about 3 centimeters (cm) to about 5 cm or more away from the needle penetration point. In some embodiments, the injection region is at least about 4 centimeters (cm) to about 5 cm or more away from the needle penetration point. In some embodiments, the injection region is at least about 0.1 centimeters (cm) to about 10 cm or more away from the needle penetration point. In some embodiments, the injection region is at least about 0.1 centimeters (cm) to about 15 cm or more away from the needle penetration point.

In some embodiments, the injection region is at least about 0.1 cm away from the needle penetration point. In some embodiments, the injection region is at least about 0.5 cm away from the needle penetration point. In some embodiments, the injection region is at least about 1 cm away from the needle penetration point. In some embodiments, the injection region is at least about 2 cm away from the needle penetration point. In some embodiments, the injection region is at least about 3 cm away from the needle penetration point. In some embodiments, the injection region is at least about 4 cm away from the needle penetration point. In some embodiments, the injection region is at least about 5 cm away from the needle penetration point. In some embodiments, the injection region is at least about 6 cm away from the needle penetration point. In some embodiments, the injection region is at least about 7 cm away from the needle penetration point. In some embodiments, the injection region is at least about 8 cm away from the needle penetration point. In some embodiments, the injection region is at least about 9 cm away from the needle penetration point. In some embodiments, the injection region is at least about 10 cm away from the needle penetration point. In some embodiments, the injection region is at least about 15 cm away from the needle penetration point.

In some embodiments, the diameter of the injection region is minimized yet still provides an adequate blood/device barrier. In some embodiments, the diameter of the injection region is minimized by providing a center column 217 of the needle assembly 211 comprising a smaller diameter. In some embodiments, the smaller center attaches on its proximal end to a proximal region of the adaptor 209 instead of attaching to the injector 201. In some embodiments, the inner diameter of the center column 217 of the needle assembly 211 does not have to be larger the exterior diameter of the distal end of the injector or syringe.

In some embodiments, the center column 217 of the needle assembly 211 is able to collapse upon the translation of the upper body 212 moving distally with respect to the lower body 256, thereby extending and exposing the needle 214 to deliver an injection. In some embodiments, upon completion of the injection, the resilient components (i.e. the distal shield spring 218, the proximal needle shield spring 270, and the inner sleeve spring 216) of the needle assembly 211 reset the position of the center column components. In some embodiments, upon completion of the injection, the resilient components (i.e. the distal shield spring 218, the proximal needle shield spring 270, and the inner sleeve spring 216) of the needle assembly 211 reset the position of the upper body 212 with respect to the lower body 256. In some embodiments, upon completion of the injection, the resilient components (i.e. the distal shield spring 218, the proximal needle shield spring 270, and the inner sleeve spring 216) of the needle assembly 211 activate the proximal needle shield 220 and the distal needle shield 264 within the needle assembly 211 so as to cover the proximal and distal aspects of the needle 214. In some embodiments, upon completion of the injection, the resilient components (i.e. the distal shield spring 218, the proximal needle shield spring 270, and the inner sleeve spring 216) of the needle assembly 211 lock the needle assembly 211 such as to prevent a user from reusing the needle assembly and/or accidentally puncturing themselves or others with the needle 214. In some embodiments, upon completion of the injection, the resilient components of the needle assembly 211, lock the needle assembly and create a barrier between the inner walls of the distal cylindrical aperture of the adaptor 209 and the patient's skin, blood, and/or other bodily fluids.

In some embodiments, the components of the center column 217 which create this resetting and/or locking mechanism include the inner sleeve 266, an aperture 222, the inner sleeve spring 216, the outer cylinder 268, the ramped track 236, the proximal needle shield 220, the proximal needle shield spring 270, the distal needle shield 264, a first distal needle shield wing 272a, a second needle shield wing 272b, and the distal needle shield spring 216.

Figure 5:
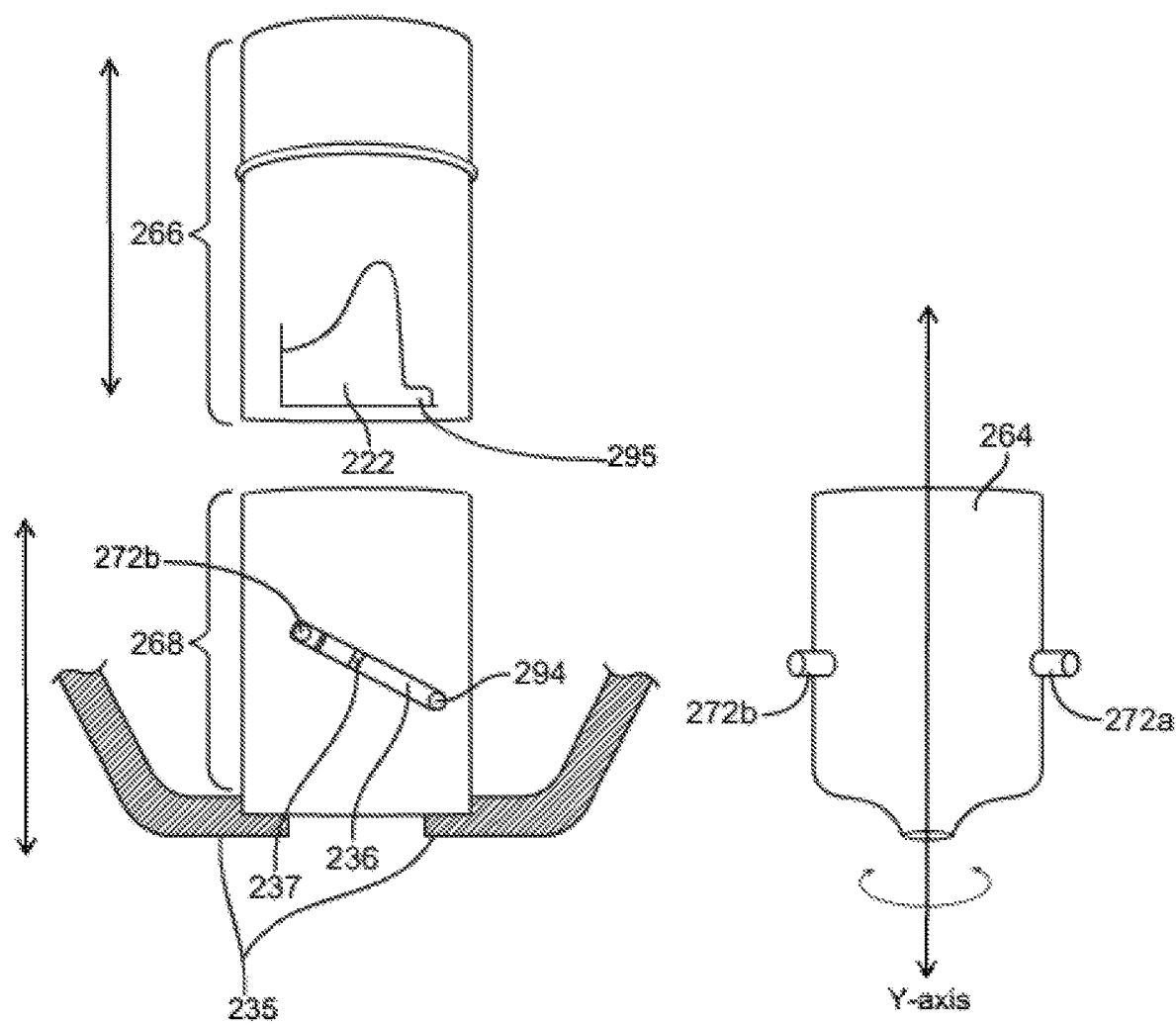
FIG. 5 depicts an embodiment of the main, inner components of the needle assembly.

FIG. 5 shows the movement and components of the inner sleeve 266, the outer sleeve 268, and the distal needle insertion shield 264. As shown in FIG. 5, the inner sleeve 266, the outer sleeve 268 only move in a longitudinal axis (i.e., they only moved distally and proximally), whereas the distal needle shield 264 is able to rotate about its axis, labeled as the Y-axis in FIG. 5. In some embodiments, the action of needle deployment, insertion, and retraction as described supra is initiated by the distal translocation of the upper body 212 with respect to the lower body 256. In some embodiments, this distal translocation the upper body 212 with respect to the lower body 256 exerts a distal force (i.e., distally presses) on the inner sleeve 266. In some embodiments, the distal force on the inner sleeve 266 causes the distal slidable translocation of the inner 266 relative to the outer sleeve 268. In some embodiments, there are two points of resistance which oppose that distal translocation: the first distal shield insertion arm 272a and the second distal shield insertion arm 272b; and the resilient element of the inner sleeve spring 216.

In some embodiments, the first distal shield insertion arm 272a and the second distal shield insertion arm 272b extend through the aperture 222. In some embodiments, the aperture 222 fully extends through the wall of the inner sleeve 266. In some embodiments, the lateral ends of the first distal shield insertion arm 272a and the second distal shield insertion arm 272b ride along a ramped track 236. In some embodiments, the ramped track 236 is created by a groove on the interior wall of the outer sleeve 268. In some embodiments, the ramped track 236 does not fully penetrate the wall of the outer sleeve 268 at any point along the ramped track. In some embodiments, the ramped track 236 has a bump 237 and a track locking notch 294. In some embodiments, the ramped track runs in a 45 degree angle relative to the plane of the active-cooling surface 235. In some embodiments, the bump 237 extends medially in the ramped track 236. In some embodiments, the bump 237 has a round proximal aspect and a vertical distal aspect. In some embodiments, from their initial position, the first distal shield insertion arm 272a and the second distal shield insertion arm 272b are advanced down the ramped track 236 due to the exerted distal force. In some embodiments, once the first distal shield insertion arm 272a and the second distal shield insertion arm 272b overcome the bumps, they are unable to be reset and the distal shield insertion arms continue down the ramped track onto the track locking notch where they are locked in position. In some cases, the distal shield insertion arms are blocked by an edge of the aperture through the wall of the inner sleeve 266. In some embodiments, the track locking notch 294 is circular. In some embodiments, the track locking notch 294 is laterally deeper in the than the rest of the ramped track. In some embodiments, the track locking notch 294 has a relative vertical wall and is set at about 90 degrees lengthwise relative to that of the outer sleeve 268. In some embodiments, once the first distal shield insertion arm 272a and the second distal shield insertion arm 272b enter the track locking notch 294 and are locked in that position, they cannot be pushed out with any amount of proximal or distal pressure on the distal shield insertion arms, on the distal needle shield 264, on the inner sleeve 266, or on the outer sleeve 268.

In some embodiments, the aperture 222 is shaped so as to push the first distal shield insertion arm 272a and the second distal shield insertion arm 272b distally upon an initial distal translocation of the inner sleeve 266. In some embodiments, the aperture 222 does not put any more pressure on the first distal shield insertion arm 272a and the second distal shield insertion arm 272b in a proximal or distal direction once the resistance of the bump 237 in the track are overcome. In some embodiments, the aperture 222 blocks the first distal shield insertion arm 272a and the second distal shield insertion arm 272b from entering the track locking notch 294 until the inner sleeve 266 returns to its resting (i.e., initial) position. In some embodiments, the aperture 222 blocks the first distal shield insertion arm 272a and the second distal shield insertion arm 272b from entering the track locking notch 294 if distal pressure is placed on the inner sleeve 266 relative to the outer sleeve 268 while the first distal shield insertion arm 272a and the second distal shield insertion arm 272b sit in their initial position. In some embodiments, a portion of the edge of the aperture 222 is immediately proximal to the first distal shield insertion arm 272a and the second distal shield insertion arm 272b while they sit in their initial position. In some embodiments, this portion of the edge applies a distal force on the distal shield insertion arms relative to the outer sleeve 268. In some embodiments, this distal force (i.e., pressure) pushes the first distal shield insertion arm 272a and the second distal shield insertion arm 272b down the ramped track 236 in a distal direction and causes polar axial turning of the distal needle shield 264. In some embodiments, the first distal shield insertion arm 272a and the second distal shield insertion arm 272b are therefore able to overcome the resistant force of the bump 237, and the distal shield insertion arms are urged the rest of the way, distally down the ramped track 236 by the distal needle shield spring 218.

In some embodiments, the shape the aperture 222, is designed such that the inner sleeve 266 is able to slide to its most distal possible position within the outer sleeve 268 without putting any more proximal or distal pressure on the first distal shield insertion arm 272a and the second distal shield insertion arm 272b. In some embodiments, the perimeter of the aperture 297 has an edge with a vertical portion and an aperture locking notch 295. In some embodiments, the vertical portion of the edge lies medial to the proximal edge of the track locking notch 294. In some embodiments, the aperture locking notch 295 extends to the other side of the track locking notch 294 in the axial direction and the height of the track locking notch 294 is greater than its diameter. In some embodiments, only when the distal needle shield insertion arms have overcome the bumps in the ramped track 236 and the inner sleeve 266 returns to its resting position, the track locking notch 294 is exposed to the interior of the inner sleeve 266 and the distal needle shield insertion arms are able to enter and stop in the track locking notches. In some embodiments, the aperture in the inner sleeve 266 initiates the movement of the distal needle shield 264, blocks it from entering the lock position until the distal pressure on the inner sleeve 266 is removed, and the resilient forces of the inner sleeve spring 216 return the inner sleeve 266 to its proximal resting position. In some embodiments, when the distal needle shield arms reach the lock position, they are resting in the aperture locking notch 294 of the inner sleeve 266. In some embodiments, this prevents the inner sleeve 266 from being compressed again; thereby preventing the reuse of the needle 214 and/or accidental needle punctures from a deployed needle. In some embodiments, as the distal needle shield arms ride along the ramped track 236, the proximal medial aspects of the distal needle shield 264 interact with a first proximal needle shield wing 290a and a second proximal needle shield wing 290b, causing the distal needle shield 264 to turn, and releasing the proximal needle shield 220. In some embodiments, the proximal needle shield 220 is subsequently held in place distally by the first proximal needle shield wing 290a and a second proximal needle shield wing 290b and proximally by a first proximal securing tab 292a and a second proximal securing tab 292b (shown in FIG. 3A).

FIG. 4 shows an exploded view of the pain-reducing injection apparatus 200. In some embodiments, the distal needle insertion shield 264 is positioned within the inner sleeve 266. In some embodiments, the inner sleeve 266 containing the distal needle insertion shield 264 is positioned within the outer sleeve 268. As shown in FIG. 4, the inner sleeve 266 comprises a first aperture 222a and a second aperture 222b. In some embodiments, the inner sleeve 266 is coaxially aligned with the outer sleeve 268. In some embodiments, the first aperture 222a and the second aperture 222b of the inner sleeve 266 are coaxially aligned with the first ramped track and the second ramped track of outer sleeve 268 (not shown in FIG. 4). In some embodiments, the proximal region of the pain-reducing injection apparatus 200 comprises an insertion activation button 208, a barrel 234, and upper body insertion wings, as shown in FIG. 4.

In some embodiments, the outer sleeve 268 comprises at least one slit (not shown in FIG. 4) configured to receive a distal needle shield insertion arm. In some embodiments, a distal needle insertion arm is inserted into at least one slit of the outer sleeve 268 when inserting the inner sleeve 266 into the outer sleeve 268. In some embodiments, the inner sleeve 266 comprises at least one slit (not shown in FIG. 4) configured to receive a distal needle shield insertion arm. In some embodiments, a distal needle insertion arm is inserted into at least one slit of the inner sleeve 266 when inserting the distal needle shield 264 into the inner sleeve 266. In some embodiments, the outer sleeve 268 comprises at least one outer sleeve ramp (not shown in FIG. 4) connecting to the ramped track, the outer sleeve ramp configured to receive a distal needle shield insertion arm and guide it towards the ramped track 236 when inserting the inner sleeve 266 into the outer sleeve 268. In some embodiments, the inner sleeve 266 comprises at least one inner sleeve ramp (not shown in FIG. 4) connecting to the aperture 222, the inner sleeve ramp configured to receive a distal needle shield insertion arm and guide it towards the aperture 222 when inserting the distal needle shield 264 into the inner sleeve 266.

In some embodiments, the distal needle shield 264 comprises a distal needle shield opening 265, as shown in FIG. 4. In some embodiments, the distal needle shield opening 265 is an opening located at a distal end of the distal needle shield 264, configured to allow the needle 214 to exit therethrough. In some embodiments, the outer sleeve 268 and the needle assembly housing 259 comprises a needle opening 269, as shown in FIG. 4. In some embodiments, the needle opening 269 is an opening located at the distal end of the needle assembly, configured to allow the needle 214 to exit therethrough.

In some embodiments, the outer sleeve 268 comprises an outer sleeve ridge 257, as shown in FIG. 3B and FIG. 4. In some embodiments, the outer sleeve 268 comprises an outer sleeve ridge 257 is configured to align the outer sleeve 268 with the inner sleeve 266. In some embodiments, the outer sleeve ridge 257 is configured to align the outer sleeve 268 with the inner sleeve 266. In some embodiments, the inner sleeve 266 comprises a first inner sleeve ridge 261a and a second inner sleeve ridge 261b, as shown in FIG. 3B and FIG. 4. In some embodiments, the first inner sleeve ridge 261a and the second inner sleeve ridge 261b are configured to align the inner sleeve 266 with the outer sleeve 268.

Needle Cap

Disclosed herein, in certain embodiments, are needle caps, comprising: a housing, the housing configured to receive a needle assembly; and a fingerprint authentication locking mechanism for selectively engaging and disengaging the needle cap from the needle assembly; wherein the fingerprint authentication locking mechanism comprises a fingerprint sensor and a needle cap lock.

In some embodiments, a needle cap comprises a sensor to identify a patient and unlock needle cap lock. In some embodiments, the sensor is a biometric sensor. In some embodiments, the pen-type injector sleeve comprises a needle cap with a patient authentication locking mechanism. In some embodiments, the needle cap is reversibly attached to a distal end of the pen-type injector sleeve. In some embodiments, the needle cap comprising a needle cap lock and a patient authentication mechanism locks and/or unlocks a needle assembly that is attached to a distal end of a pen-type injector sleeve. In some embodiments, the patient authentication mechanism is a biometric sensor authentication mechanism. Non-limiting examples of the biometric sensor includes a fingerprint sensor, a face recognition device, and a retinal scanner.

In some embodiments, the fingerprint sensor is located on the needle cap. In some embodiments, the fingerprint sensor is located on the pain-reducing injection apparatus housing. In some embodiments, the needle cap lock is unlocked upon recognition of a fingerprint of a user by the fingerprint sensor. In some embodiments, the needle cap lock is unlocked upon recognition of a bar code or electronic identification tag. In some embodiments, the needle cap comprises a power source operatively coupled to the fingerprint sensor and needle cap lock. In some embodiments, the needle cap comprises an iris scanner. In some embodiments, the needle cap lock is unlocked upon recognition of a patient's iris by the iris scanner. In some embodiments, the needle cap comprises an facial recognition device. In some embodiments, the needle cap lock is unlocked upon recognition of a patient's face by the facial recognition device.

In some embodiments, the needle cap comprises a barcode reader that identifies and/or tracks the needle cap, a pain-reducing injection apparatus housing, a pain-reducing injection apparatus, and/or a syringe. In some embodiments, the needle cap, a pain-reducing injection apparatus housing, a pain-reducing injection apparatus, and/or a syringe comprise a label or a barcode. In some embodiments, the label or barcode is scanned prior to delivering a medicament to a patient, prior to loading a drug delivery device, and/or prior to removing the needle cap. Alternatively, in some embodiments, the needle cap includes a radiofrequency identification (RFID) unit, memory, or chip for identifying and/or tracking the needle cap, pain-reducing injection apparatus housing, a pain-reducing injection apparatus, and/or a syringe. In some embodiments, the RFID, memory, or chip includes a communications interface for permitting communication to or from a reader.

In some embodiments, the needle cap comprises a retinal scanner that uses ocular-based biometric technology to identify a patient's iris. In some embodiments, the retinal scanner scans a patient's iris and unlocks a needle cap lock upon successful recognition of a patient's iris.

Figure 6:
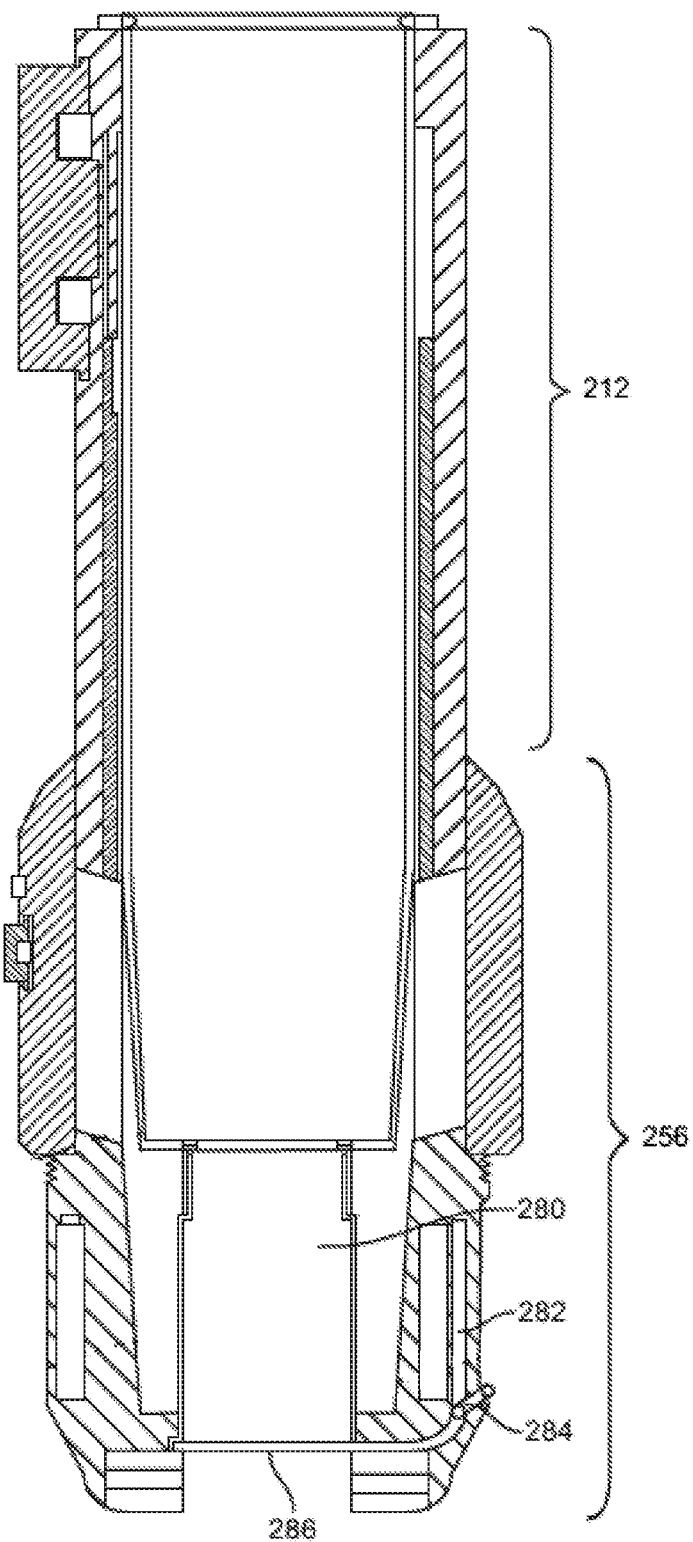
FIG. 6 depicts an embodiment of a pain-reducing injection apparatus comprising a sleeve, without a needle assembly.

FIG. 6 shows yet another example of an embodiment designed to protect a needle, a needle assembly, or a distal end of an injector. FIG. 6 shows a cap cover 286 that is configured to be opened or closed by the cap cover control tab 284. In some embodiments, the cap cover control tab 284 is configured to insert into a cap cover recess 282 when controlling the position of the cap cover 286. In some embodiments, the cap cover control tab 284 is manually or automatically controlled.

Figure 7:
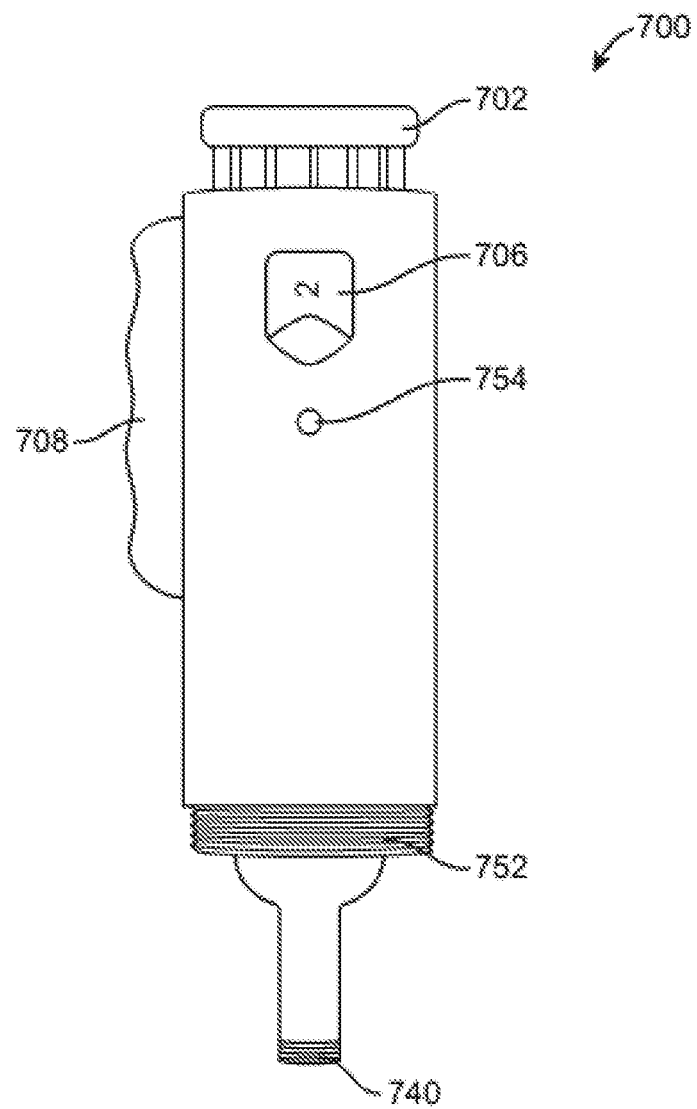
FIG. 7 depicts an embodiment of a pain-reducing injection apparatus.

FIG. 7 shows a front view of a pain-reducing injection apparatus with an enclosed, non-removable injector 700. In some embodiments, the pain-reducing injection apparatus 700 comprises an activation button 708, a light indicator 754, a thread 752 configure to receive a needle assembly, a tip 740 comprising an active-cooling surface, a unit dose display 706, and a dial 702.

Methods

Further disclosed herein, in certain embodiments, are methods of using a pain-reducing apparatus, comprising: obtaining the pain-reducing injection apparatus with a drug delivery device loaded therein, cooling the active-cooling surface using the thermoelectric cooling system, contacting the injection region with the active-cooling surface of the pain-reducing injection apparatus, inserting a needle of the drug delivery device into the injection region, and delivering a medicament into the injection region of the individual.

Disclosed herein, in certain embodiments, are methods of using a pain-reducing apparatus, comprising: obtaining the pain-reducing injection apparatus with a drug delivery device loaded therein, activating a vibration using the vibrator, contacting the injection region with the distal surface of the pain-reducing injection apparatus, inserting a needle of the drug delivery device into the injection region, and delivering a medicament into the injection region of the individual.

Additionally disclosed herein, in certain embodiments, are methods of using a pain-reducing apparatus, comprising: obtaining the pain-reducing injection apparatus with a drug delivery device loaded therein, cooling the active-cooling surface using the thermoelectric cooler, activating a vibration using the vibrator, contacting the injection region with the active-cooling surface of the pain-reducing injection apparatus, inserting a needle of the drug delivery device into the injection region, and delivering a medicament into the injection region of the individual.

Further disclosed herein, in certain embodiments, are methods of using a pain-reducing apparatus, comprising: obtaining the pain-reducing injection apparatus with a drug delivery device loaded therein, applying a force distally on the drug delivery device, the force translating distally onto the outer sleeve and the inner sleeve causing the needle to be deployed, inserting the needle into the injection region, and delivering a medicament into the injection region of the individual.

Disclosed herein, in certain embodiments, are methods comprising delivering or providing a pain-reducing injection apparatus. Additionally disclosed herein, in certain embodiments, are methods of activating cooling or activating vibration in a pain-reducing injection apparatus, comprising cooling a surface of the device using a thermoelectric cooler, activating vibration in the device using a vibrator, loading a drug delivery device into the pain-reducing injection apparatus, and loading a needle assembly into the pain-reducing injection apparatus.

Disclosed herein, in certain embodiments, are methods comprising delivering or providing a needle assembly. Further disclosed herein, in certain embodiments, are methods of activating cooling or activating vibration in a needle assembly, comprising cooling a surface of the device using a thermoelectric cooler, activating vibration in the device using a vibrator, and loading the needle assembly into a pain-reducing injection apparatus or a pen injector.

The foregoing merely illustrates the principles of the present invention. Therefore, it will be appreciated that those skilled in the art will be able to devise numerous alternative arrangements that, while not shown or described herein, embody the principles of the present invention and are thus within the spirit and scope of the invention.

EXAMPLES

Example 1—Administration of Insulin with a Pain-Reducing Injection Apparatus

A patient with diabetes type I loads a pen-type injector into the pen-type injector sleeve of the pain-reducing injection apparatus. The patient then screws in the disposable needle assembly comprising a safety mechanism into the distal end of the pain-reducing injection apparatus. The patient turns on a thermoelectric cooler of the pain-reducing injection apparatus and waits for about 1 minute until the pain-reducing injection apparatus reaches a desired temperature of 10 degrees Celsius. The patient knows the desired temperature is reached because the pain-reducing injection apparatus alerts her by turning on an indicator light and emitting a beeping sound. The patient then turns on the vibrator of the pain-reducing injection apparatus and places the active-cooling surface of the pain-reducing injection apparatus in thermal contact with the injection region located on her abdomen. The patient maintains the pain-reducing injection apparatus in contact with the injection region for about 1 minute then depresses the insertion activation button to deploy the needle. The insulin contained in the pain-reducing injection apparatus is delivered into the injection region. The patient experiences a needle-insertion pain of about a 2 on a pain scale of 1 to 10, 1 being least painful and 10 being the most painful, when compared to a delivery of insulin using a pen-type injector without cooling and vibration features. The pain-reducing injection apparatus reduces pain insertion needle.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A needle assembly, comprising:
   a. a needle;
   b. an outer sleeve having a first inner surface comprising a ramped track, and a first outer surface;
   c. an inner sleeve positioned within the outer sleeve, the inner sleeve comprising:
      a second inner surface,
      a second outer surface facing the first inner surface, and
      an aperture comprising a perimeter and a perimeter wall extending between the second inner surface and the second outer surface along the perimeter, and having a first end and a second end, and wherein the perimeter of the aperture has an aperture locking notch positioned at the second end of the aperture; and
   d. a distal needle insertion shield coaxially aligned with the inner sleeve and with the outer sleeve, the distal needle insertion shield comprising a distal shield insertion arm configured to travel along the perimeter of the aperture in contact with the perimeter wall of the aperture as the distal needle insertion shield rotates about its axis, and wherein the distal shield insertion arm extends through the aperture and is configured to travel within and along the ramped track as the distal needle insertion shield is axially rotated about the axis,
   wherein the ramped track has a track locking notch positioned at a finish of the ramped track.

2. The needle assembly of claim 1, wherein the ramped track has a start and a finish and a bump positioned medially therebetween.

3. The needle assembly of claim 2, wherein the distal shield insertion arm travels from the start of the ramped track to the finish of the ramped track as the distal needle insertion shield is axially rotated about the axis.

4. The needle assembly of claim 3, wherein the bump prevents the distal shield insertion arm to travel from the finish to the start of the ramped track once the distal shield insertion arm overcomes the bump.

5. The needle assembly of claim 4, wherein deployment of the needle from the needle assembly causes the distal shield insertion arm to overcome the bump and subsequently rest within the track.

6. The needle assembly of claim 1, wherein the aperture locking notch is aligned with the track locking notch.

7. The needle assembly of claim 6, wherein the ramped track is angled.

8. The needle assembly of claim 1, wherein the track locking notch is configured to lock the distal shield insertion arm in place after the needle is deployed and retracted.

9. The needle assembly of claim 8, wherein the ramped track is angled at an angle of about 45 degrees with respect to the distal surface of the housing.

10. The needle assembly of claim 1, wherein the first end of the aperture aligns with a start of the ramped track and the second end of the aperture aligns with a finish of the ramped track prior to deployment of the needle.

11. The needle assembly of claim 1, wherein the perimeter of the aperture has a sloped region originating from the first end of the aperture and ending at a vertical region of the aperture.

12. The needle assembly of claim 11, wherein the vertical region of the aperture originates from a peak of the sloped region and ends at the aperture locking notch.

13. The needle assembly of claim 11, wherein the deployment of the needle causes the distal shield insertion arm to rest at the peak of the sloped region, on the perimeter of the aperture.

14. The needle assembly of claim 1, wherein the aperture locking notch is configured to lock the distal shield insertion arm in place after the needle is deployed and retracted.

15. The needle assembly of claim 1, wherein the distal shield insertion arm travels from the first end of the aperture to the second end of the aperture as the distal needle insertion shield is axially rotated about the axis.

16. The needle assembly of claim 1, wherein the distal shield insertion arm rests on the perimeter of the aperture at the first end of the aperture and within the ramped track at a start of the ramped track prior to deployment of the needle.

17. The needle assembly of claim 1, wherein the needle is contained within the inner sleeve prior to deployment.

18. The needle assembly of claim 1, wherein the ramped track is unidirectional.

19. The needle assembly of claim 1, wherein the distal shield insertion arm is moved distally as the distal needle insertion shield is axially rotated about the axis.

20. A needle assembly, comprising:
   a. a needle;
   b. an outer sleeve having a first inner surface comprising a ramped track, and a first outer surface;
   c. an inner sleeve positioned within the outer sleeve, the inner sleeve comprising:
      a second inner surface,
      a second outer surface facing the first inner surface, and
      an aperture comprising a perimeter and a perimeter wall extending between the second inner surface and the second outer surface along the perimeter, and having a first end and a second end, and wherein the perimeter of the aperture has an aperture locking notch positioned at the second end of the aperture; and
   d. a distal needle insertion shield coaxially aligned with the inner sleeve and with the outer sleeve, the distal needle insertion shield comprising a distal shield insertion arm configured to travel along the perimeter of the aperture in contact with the perimeter wall of the aperture as the distal needle insertion shield rotates about its axis, and wherein the distal shield insertion arm extends through the aperture and is configured to travel within and along the ramped track as the distal needle insertion shield is axially rotated about the axis, and
   wherein the first end of the aperture aligns with a start of the ramped track and the second end of the aperture aligns with a finish of the ramped track prior to deployment of the needle.

* * * * *